(12) United States Patent
Werner

(10) Patent No.: US 9,872,701 B2
(45) Date of Patent: Jan. 23, 2018

(54) RETRACTABLE DEVICE

(71) Applicant: Richard S. Werner, Minneapolis, MN (US)

(72) Inventor: Richard S. Werner, Minneapolis, MN (US)

( * ) Notice: Subject to any disclaimer, the term of this patent is extended or adjusted under 35 U.S.C. 154(b) by 0 days.

(21) Appl. No.: 15/398,296

(22) Filed: Jan. 4, 2017

(65) Prior Publication Data

US 2017/0112521 A1   Apr. 27, 2017

Related U.S. Application Data

(63) Continuation of application No. PCT/US2016/024242, filed on Mar. 25, 2016.

(60) Provisional application No. 62/139,297, filed on Mar. 27, 2015.

(51) Int. Cl.
*A61B 17/3211* (2006.01)
*A61B 17/3213* (2006.01)
*A61B 90/00* (2016.01)
*A61B 17/00* (2006.01)

(52) U.S. Cl.
CPC ...... *A61B 17/3211* (2013.01); *A61B 17/3213* (2013.01); *A61B 2017/00477* (2013.01); *A61B 2017/32113* (2013.01); *A61B 2090/0811* (2016.02)

(58) Field of Classification Search
CPC ............ A61B 17/3211; A61B 17/3213; A61B 2090/0811; A61B 2017/32113; A61B 2017/00477
See application file for complete search history.

(56) References Cited

U.S. PATENT DOCUMENTS

| 413,225 | A | * | 10/1889 | Coates | .................... B26B 5/001 |
| | | | | | 279/51 |
| 3,657,812 | A | * | 4/1972 | Lee | .......................... B26B 1/08 |
| | | | | | 30/162 |
| 4,337,576 | A | * | 7/1982 | Drost | ................. A61B 17/3213 |
| | | | | | 30/162 |
| 5,250,063 | A | | 10/1993 | Abidin | |

(Continued)

FOREIGN PATENT DOCUMENTS

WO   WO 2016/160581 A1 * 10/2016

OTHER PUBLICATIONS

International Search Report issued for PCT/US2016/024242, dated Jul. 25, 2016, 4 pages.

*Primary Examiner* — Hwei C Payer
(74) *Attorney, Agent, or Firm* — Hamre, Schumann, Mueller & Larson, P.C.

(57) ABSTRACT

A retractable device includes a sheath member having an interior space; a retractable member disposed in the interior space of the sheath member and moveable longitudinally between an exposed position and a guarded position relative to the sheath member; a biasing member disposed longitudinally within the retractable member; and a latch member that locks the retractable member relative to the sheath member in the guarded position. In such circumstances, the latch member includes a release button extending through both the retractable and the sheath members. The retractable member is movable from the exposed position to the guarded position in response to the release button being pushed by a user.

14 Claims, 23 Drawing Sheets

(56) References Cited

U.S. PATENT DOCUMENTS

| | | | | |
|---|---|---|---|---|
| 5,292,329 A * | 3/1994 | Werner | ............. | A61B 17/3211 |
| | | | | 30/162 |
| 5,403,337 A * | 4/1995 | Platts | ................ | A61B 17/3213 |
| | | | | 30/151 |
| 5,423,843 A * | 6/1995 | Werner | ............. | A61B 17/3211 |
| | | | | 30/162 |
| 5,620,453 A | 4/1997 | Nallakrishnan | | |
| 5,779,724 A | 7/1998 | Werner | | |
| 8,943,700 B2 * | 2/2015 | Cetola | ................ | A61B 17/3213 |
| | | | | 30/162 |
| 2009/0216258 A1 | 8/2009 | Geuder | | |
| 2010/0146799 A1 | 6/2010 | Hoffman | | |
| 2014/0182140 A1 | 7/2014 | Penblade | | |
| 2017/0112521 A1* | 4/2017 | Werner | ............. | A61B 17/3213 |

* cited by examiner

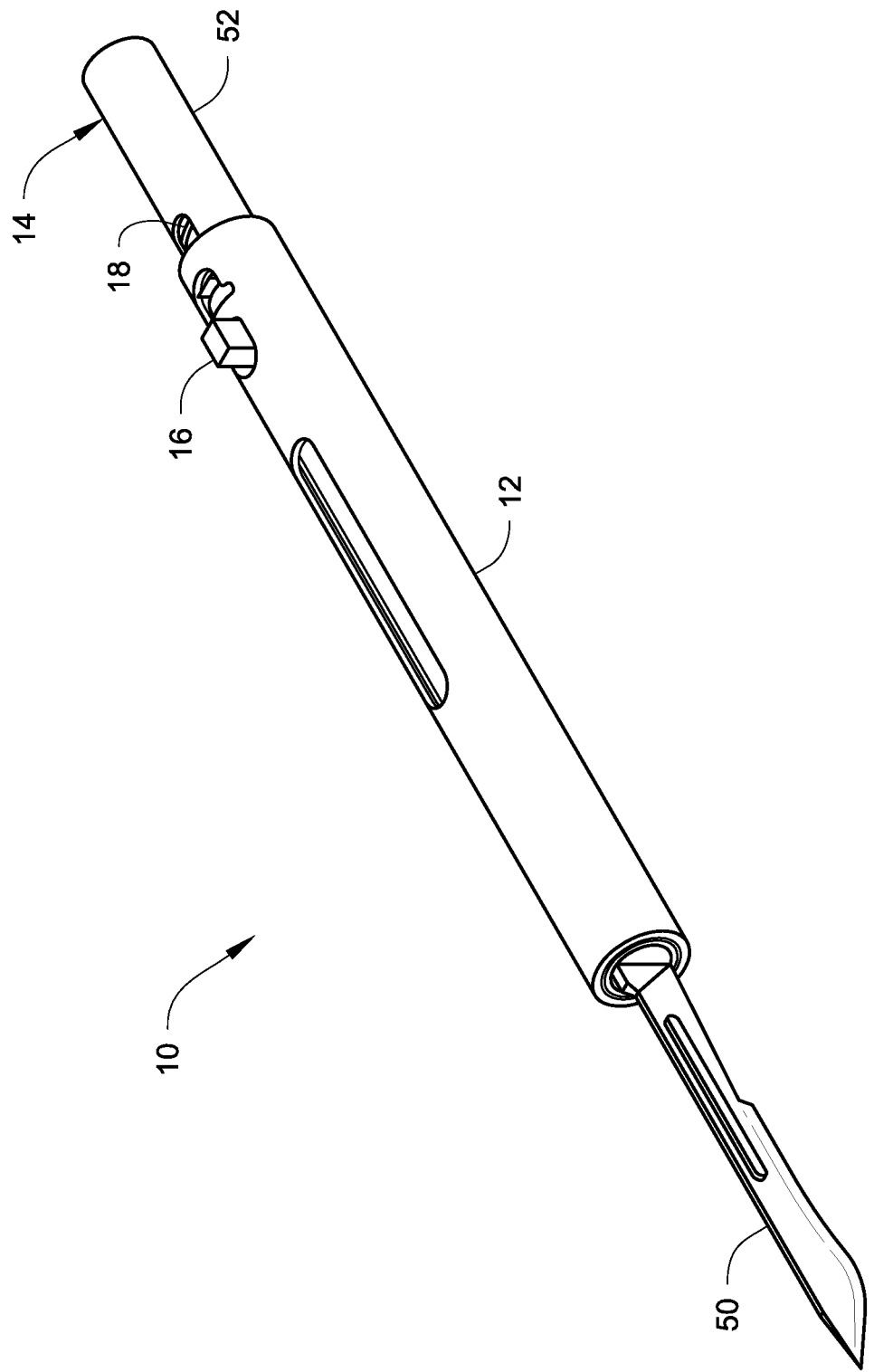

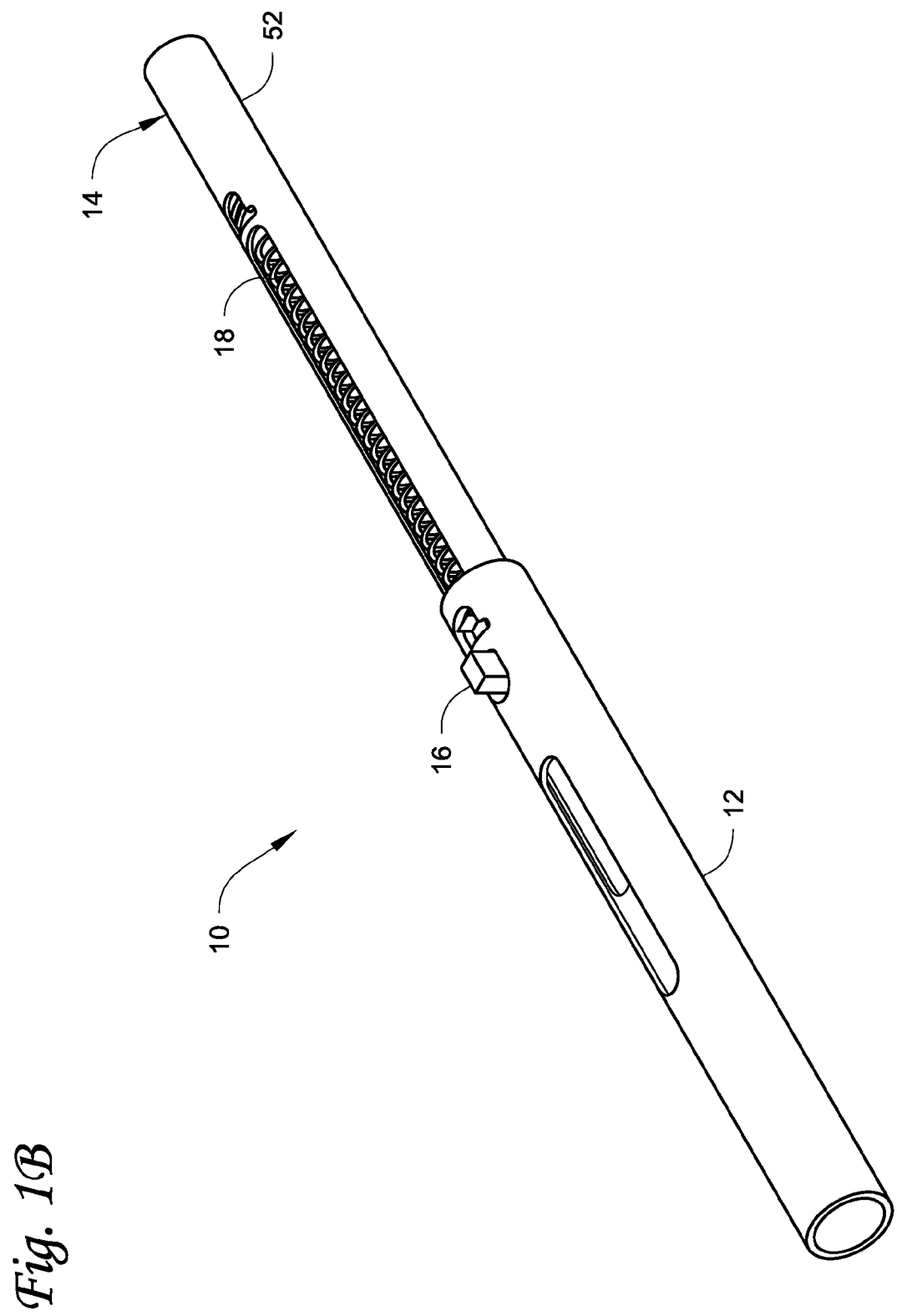

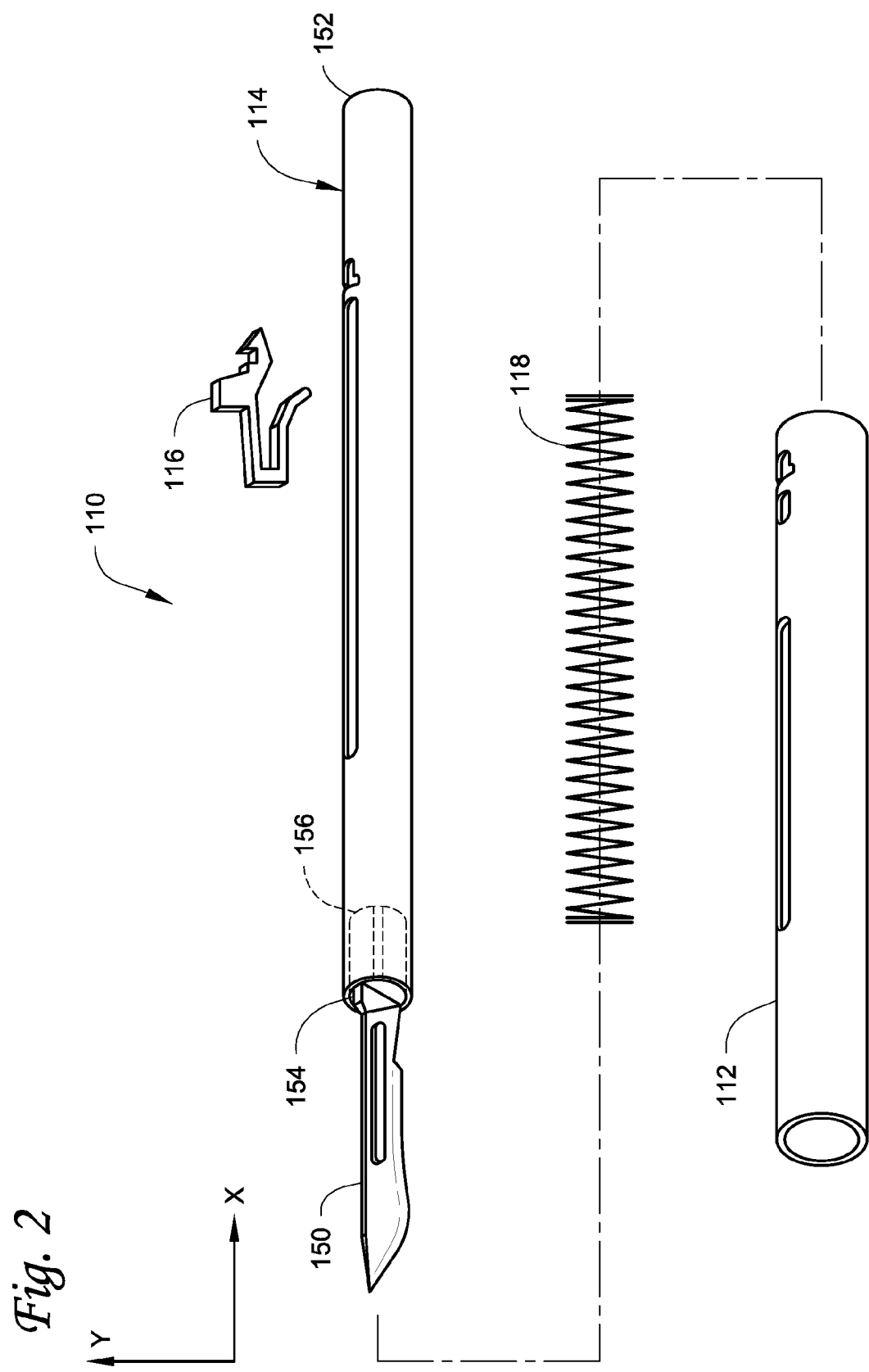

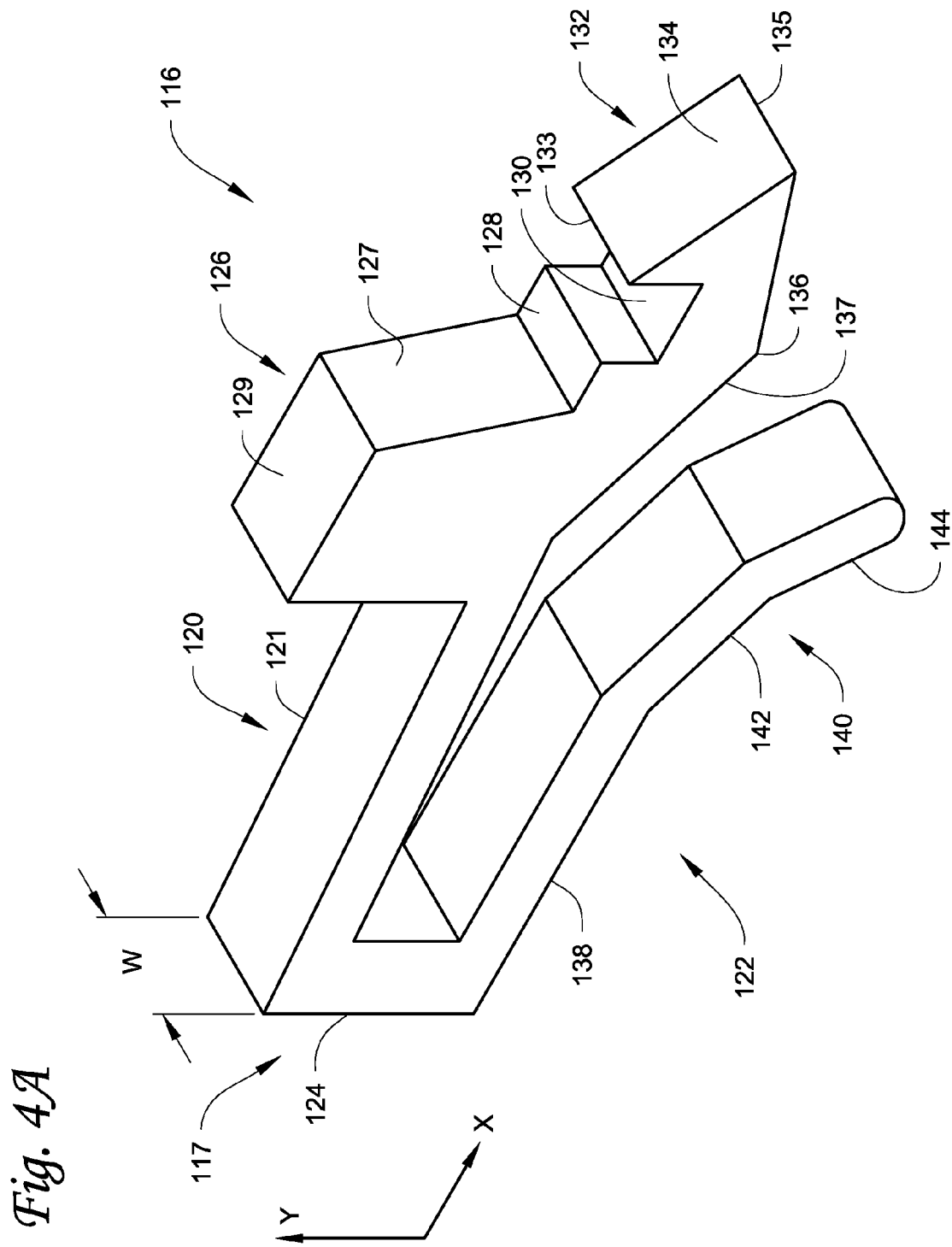

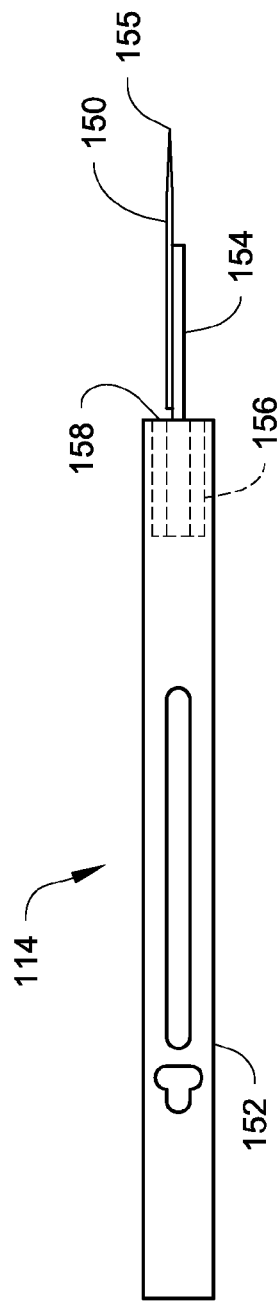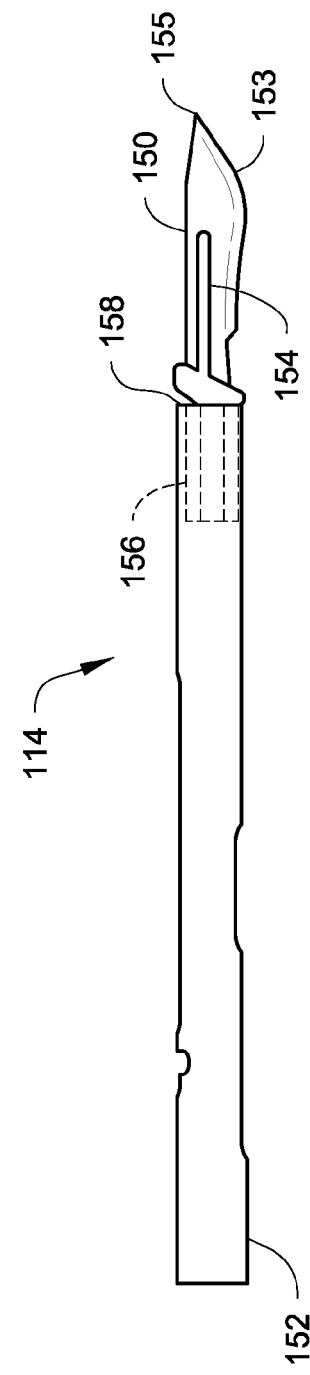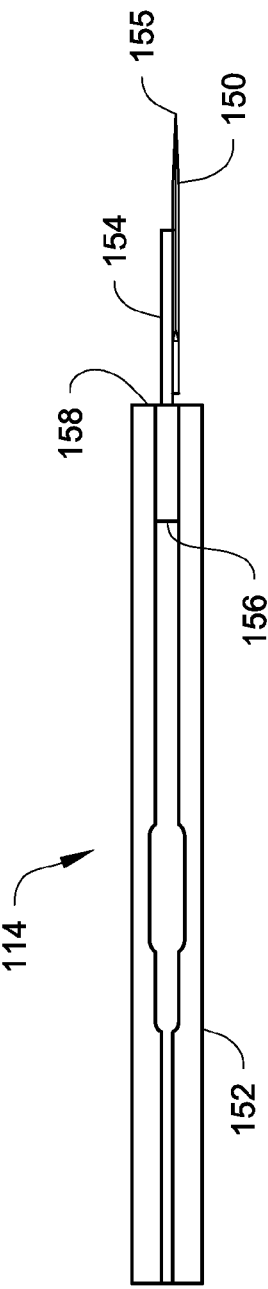
Fig. 5A
Fig. 5B
Fig. 5C

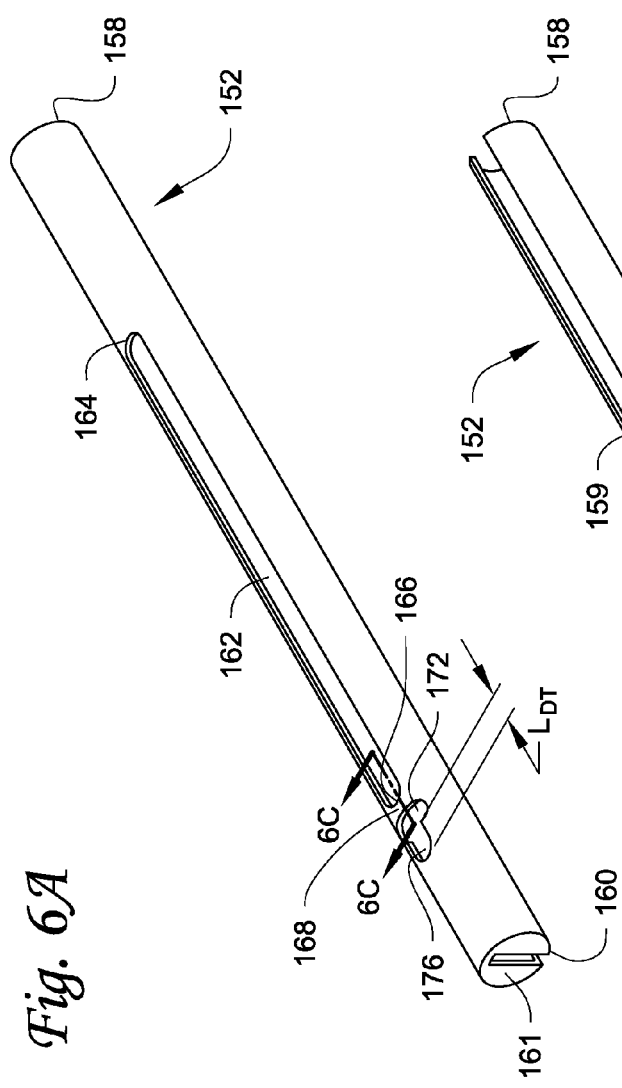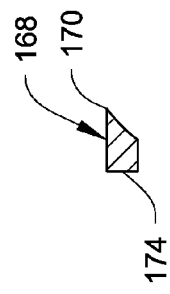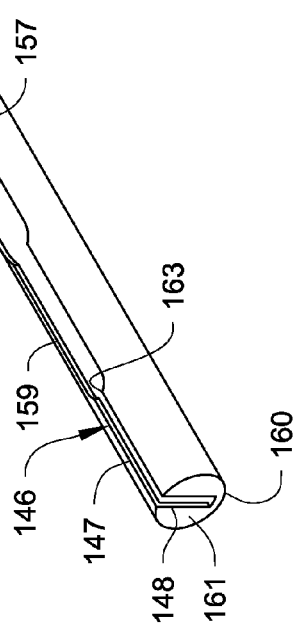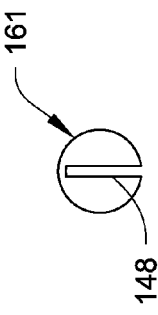

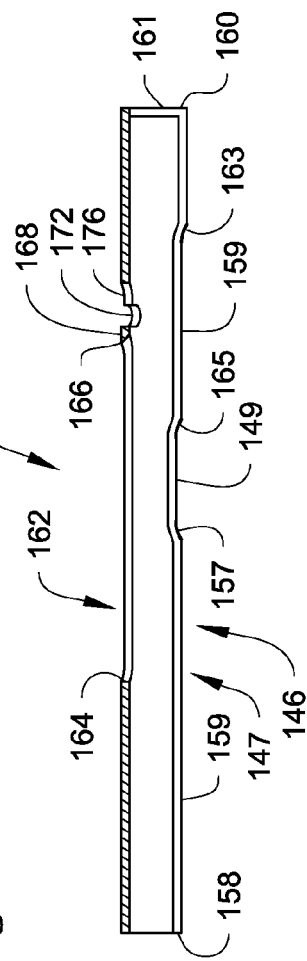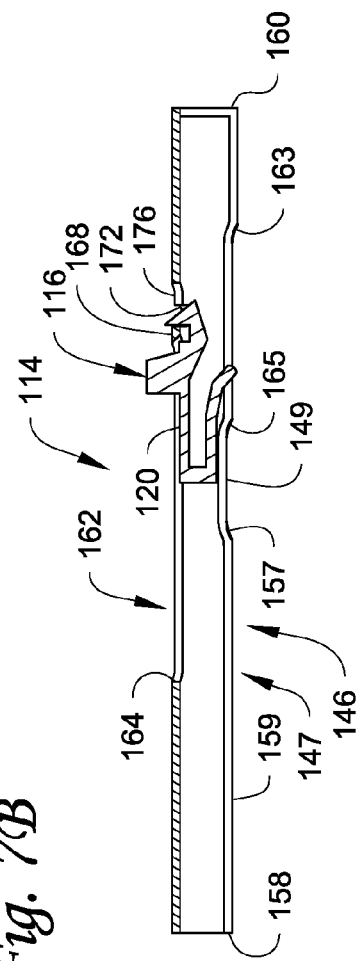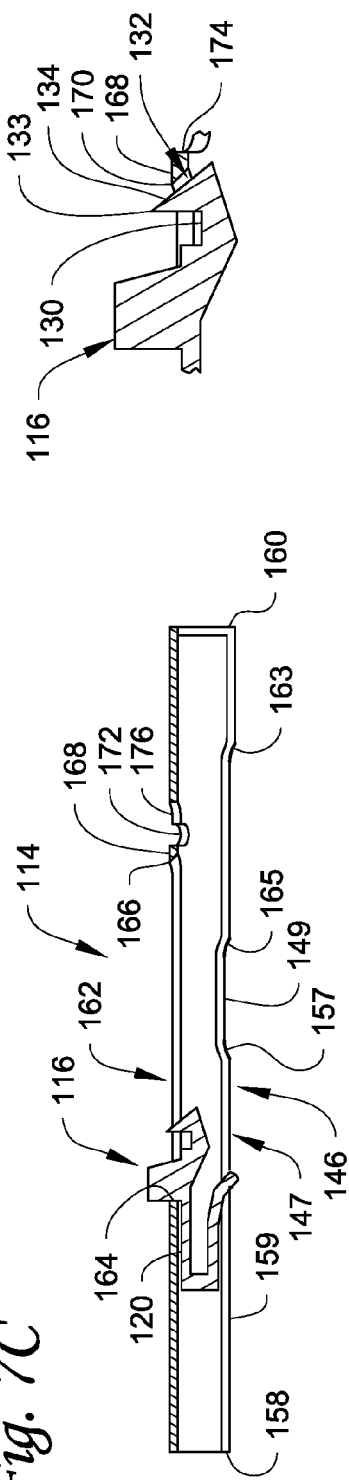

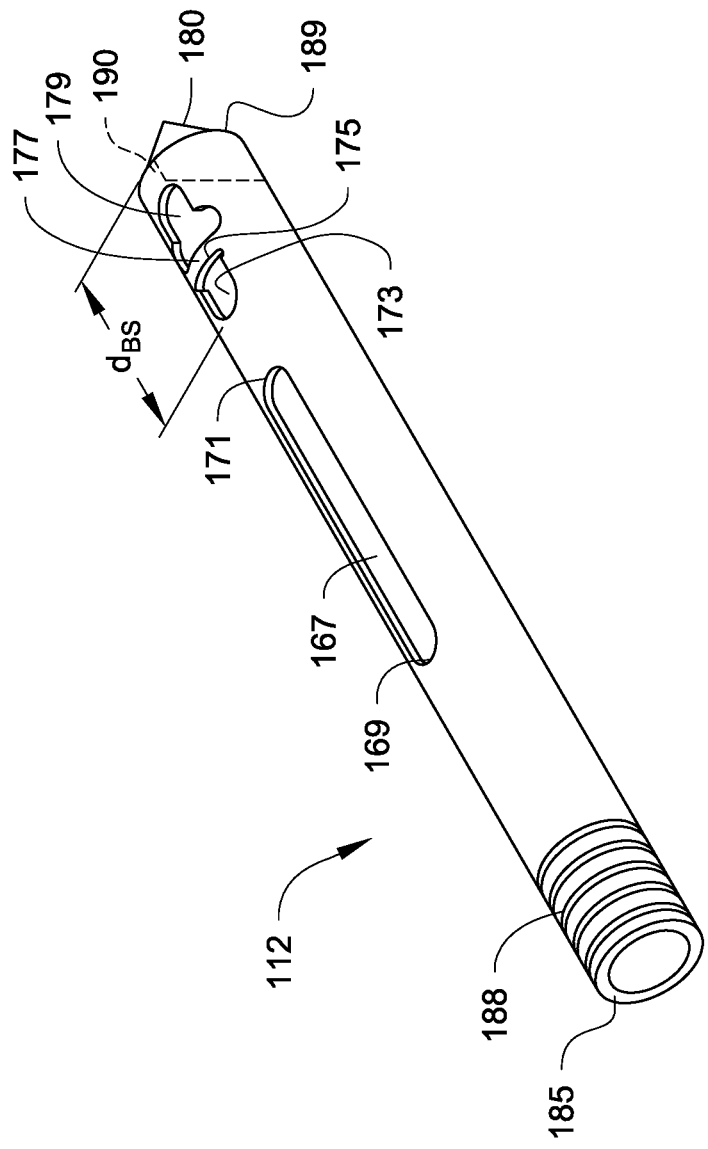

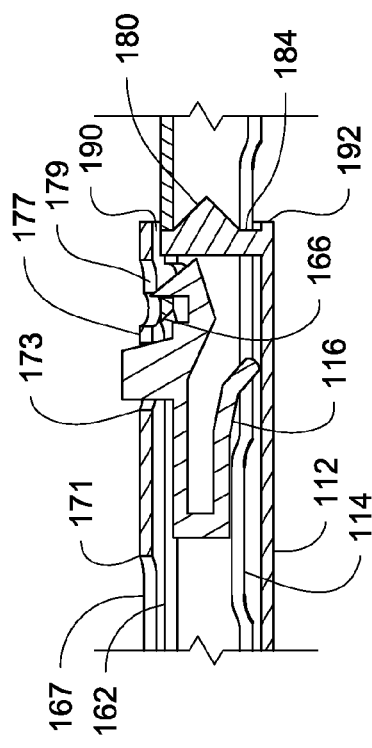
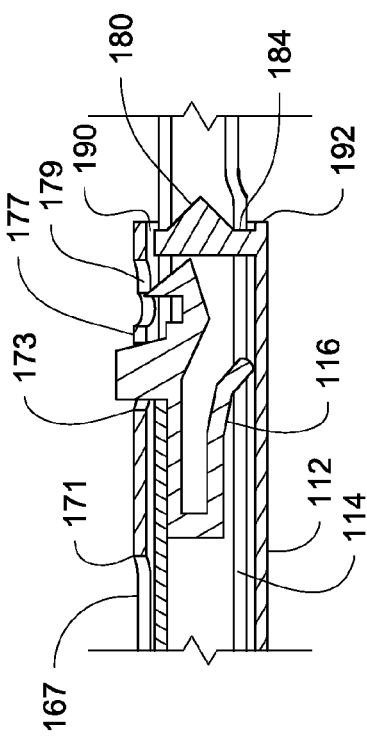
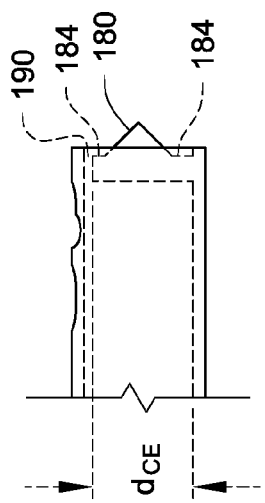
Fig. 8B
Fig. 8C
Fig. 8D

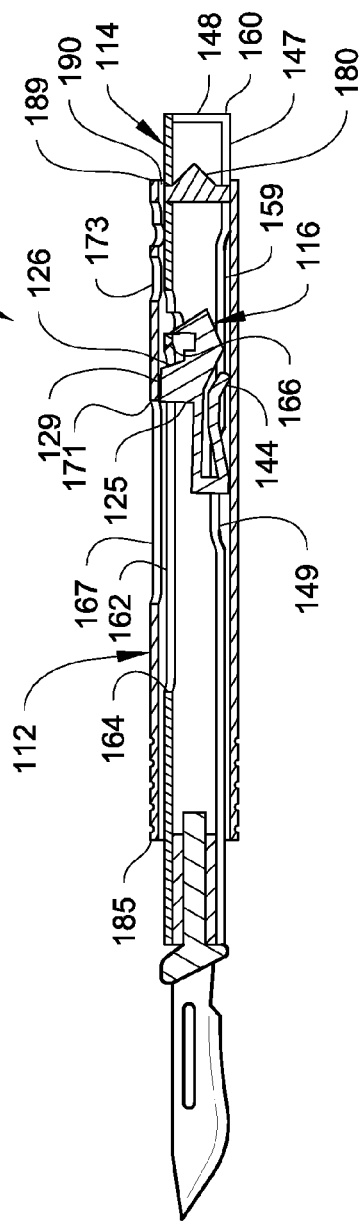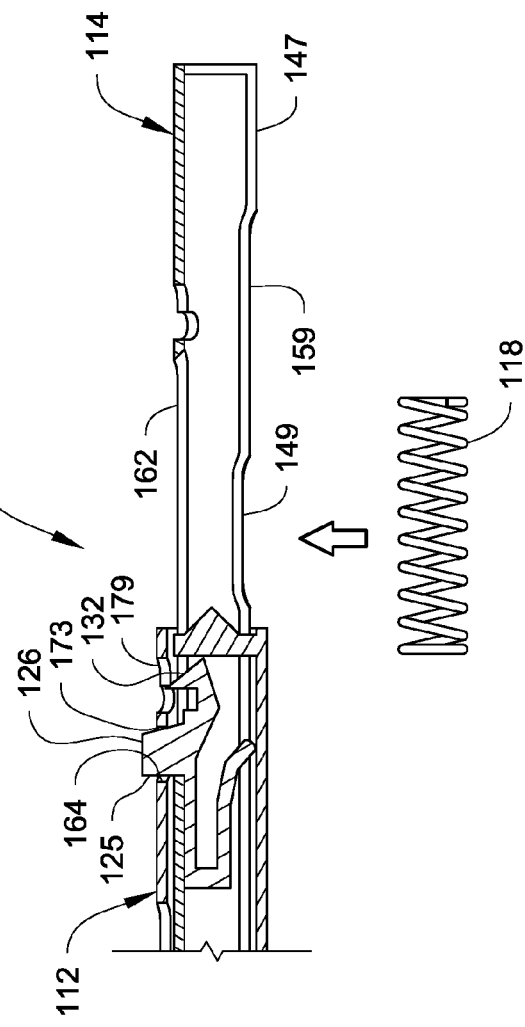
Fig. 10A
Fig. 10B

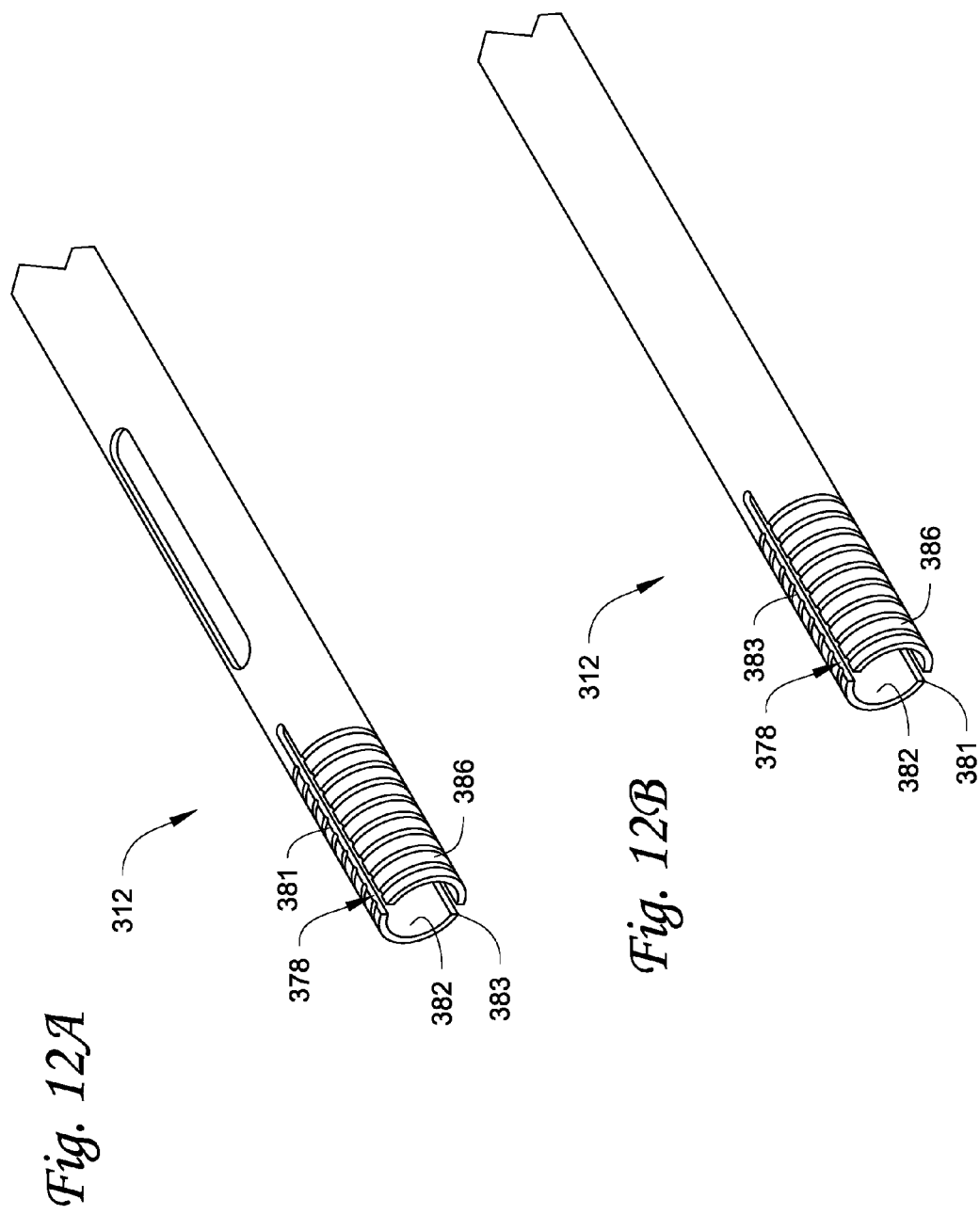

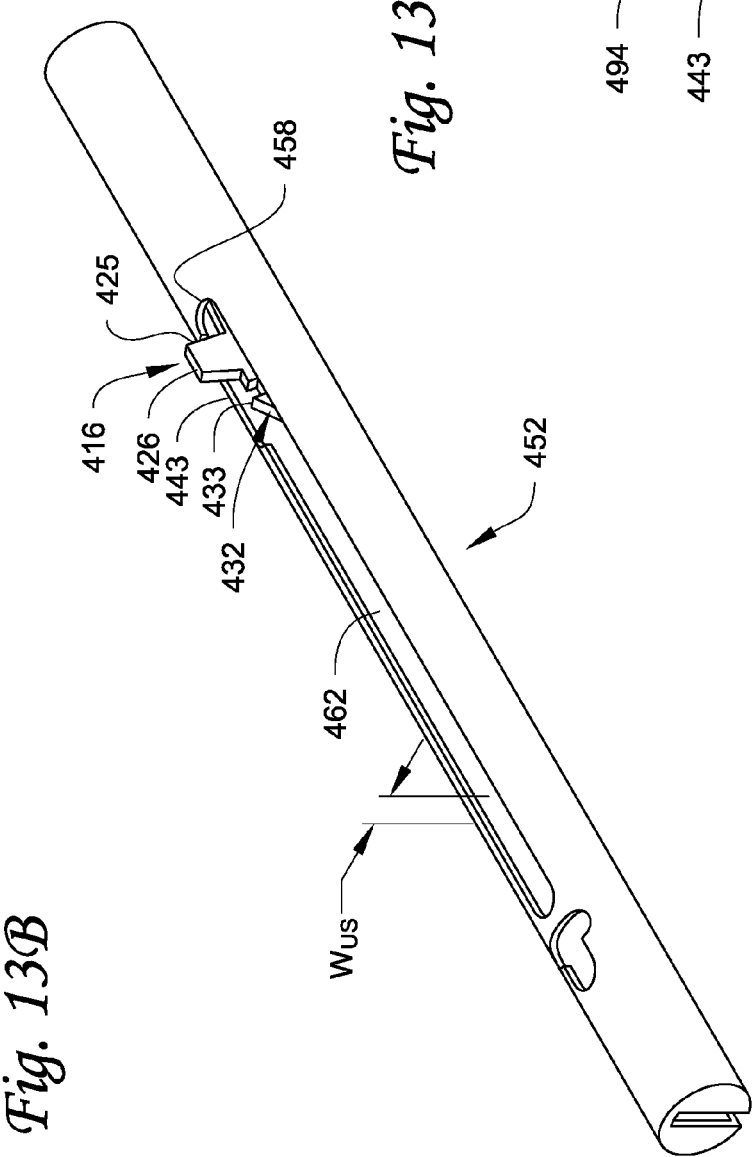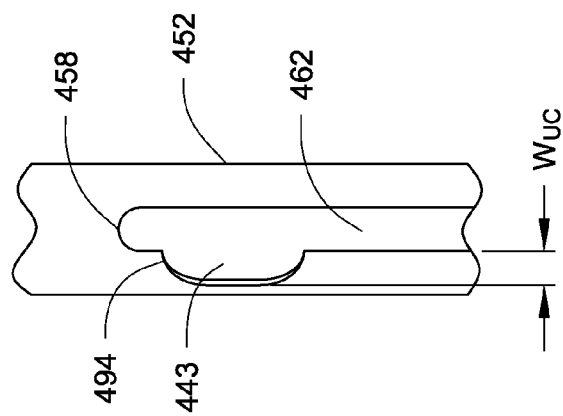

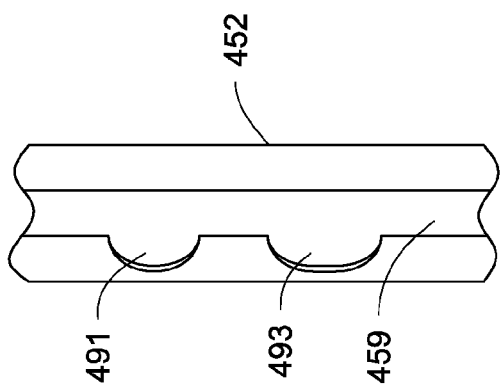
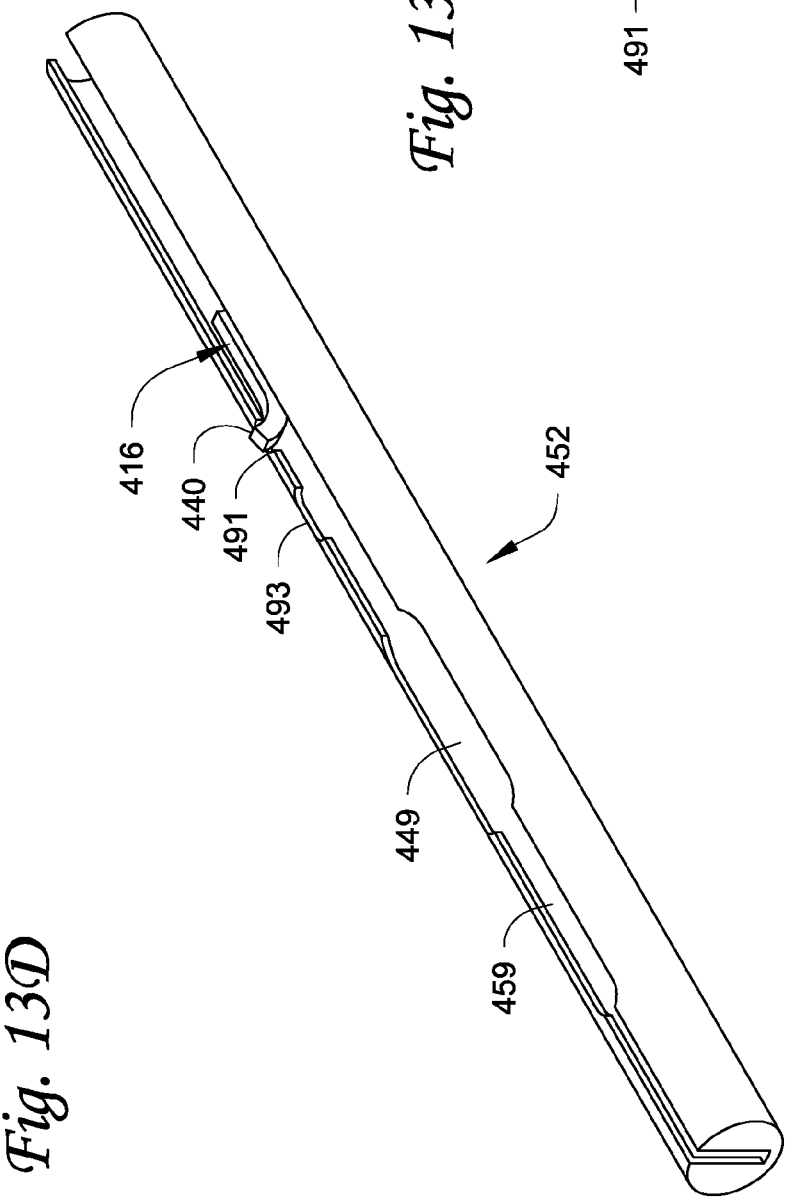

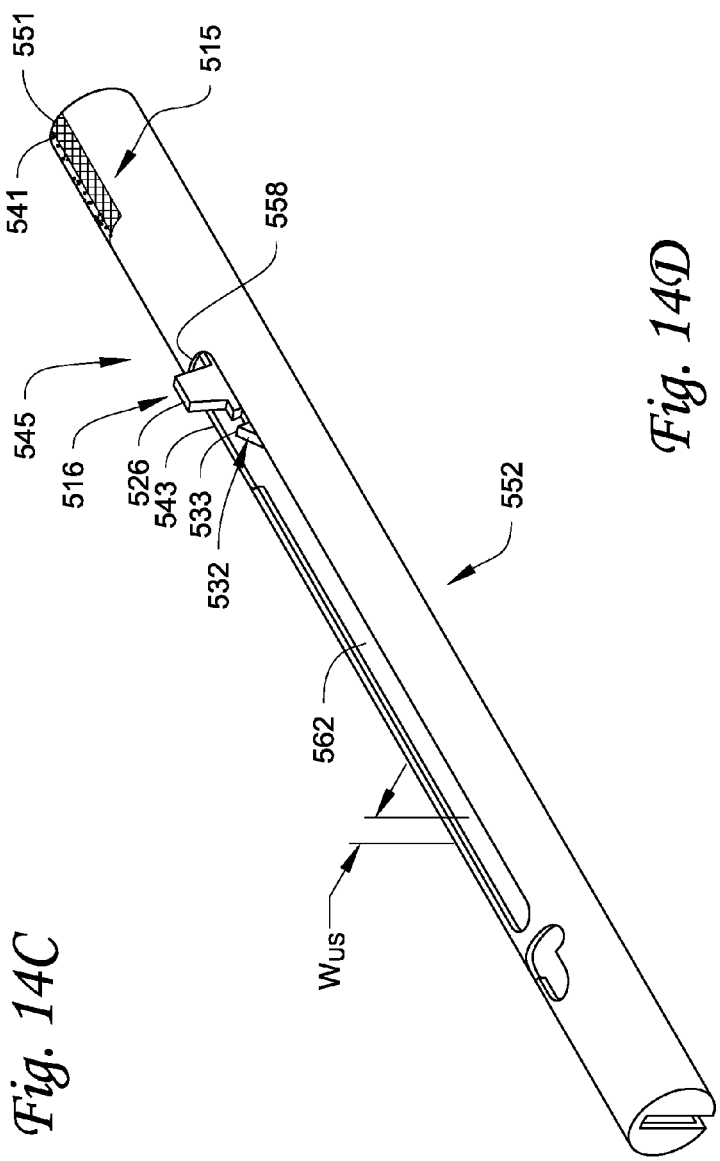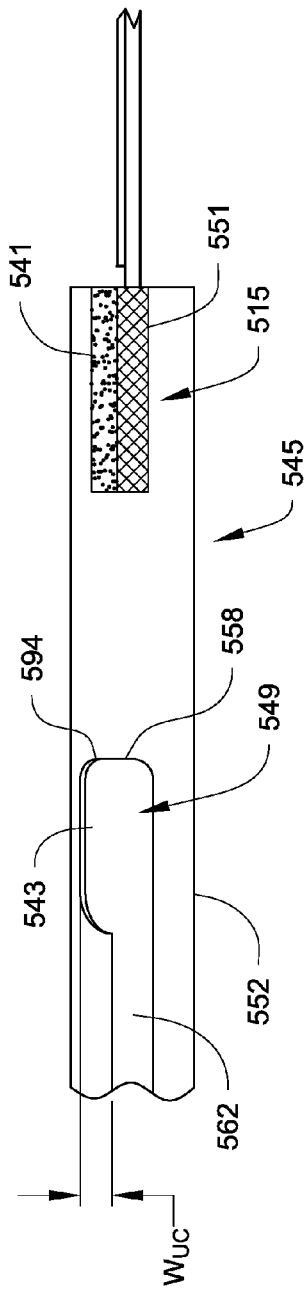

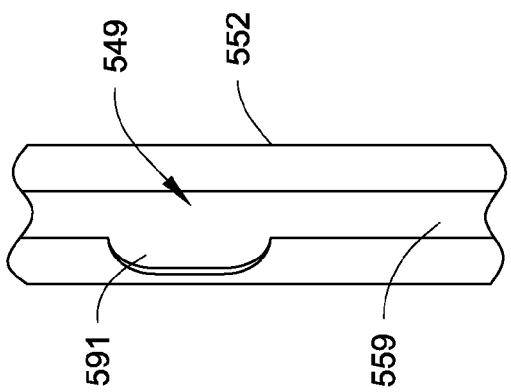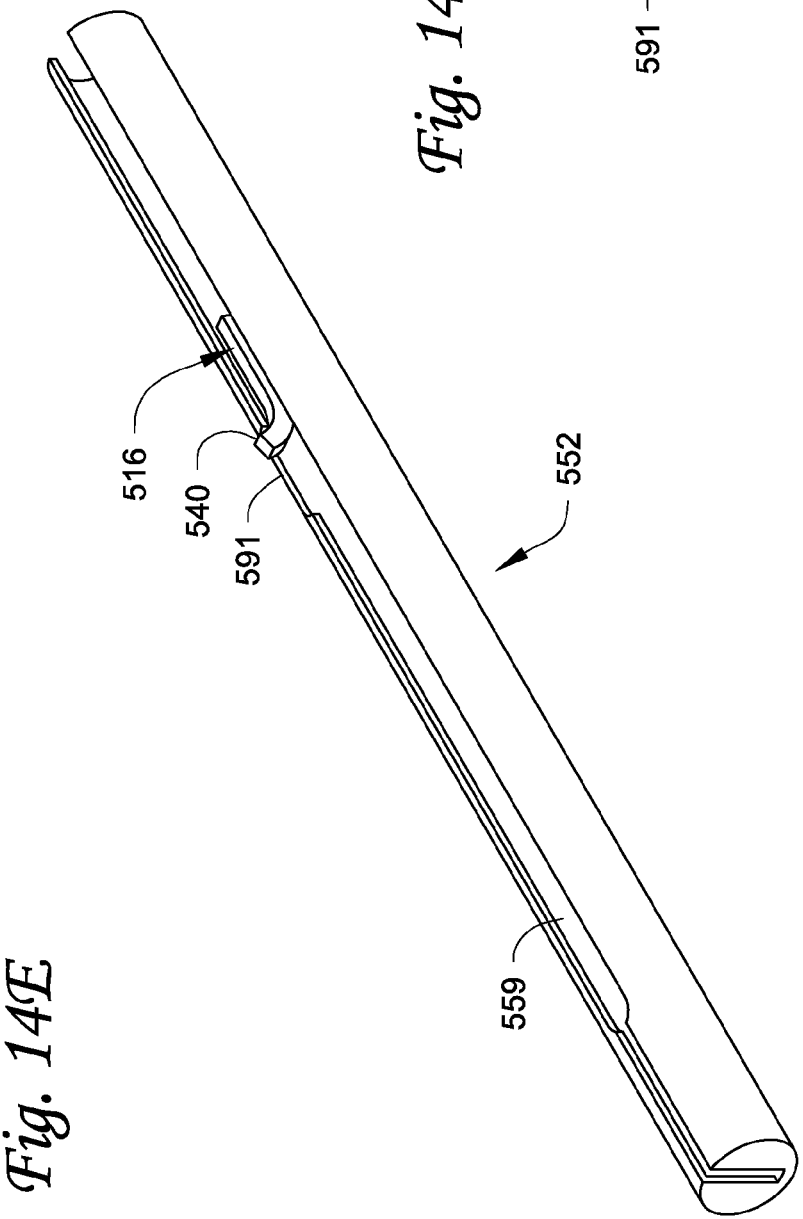

RETRACTABLE DEVICE

FIELD

The present invention relates generally to retractable devices that can be positioned in a guarded position and an exposed position.

BACKGROUND

Scalpels are a class of knives used in the surgical environment for a variety of uses including incising, stabbing and shaving human and animal skin and tissues. Conventional scalpels used for this purpose have a stationary blade. The blade is always exposed thereby creating a hazard of inadvertent puncture to an operating room team member or to any other person who may come in contact with a scalpel, especially who may come in contact with a used scalpel. For example, in some emergency situations, a surgeon must work quickly and hand instruments back and forth to assistants. It is dangerous sometimes because the sharp scalpels can accidentally cut or jab the personnel's hands during the operation. Certain fatal infections can be transferred to individuals through small cuts. The primary hazard of skin puncture is the possible transmission of an infectious agent, such as H.I.V., hepatitis B. and hepatitis C. The sequelae of scalpel injuries are emotionally traumatic and potentially expensive for the institution involved. In the operating room, scalpels cause 18% of injuries. Reusable scalpels, which require blade removal in order to reuse the handle, cause more than twice as many injuries as disposable scalpel.

To reduce injuries from scalpel blades, a variety of strategies are needed that address the different mechanisms of scalpel injuries. The use of a retractable scalpel in the operating room will eliminate the simultaneous handling of sharps by two people. Thus, scalpels with retractable blades that can be placed in a protective position during passing of the device and after use have the potential to prevent a large proportion of scalpel injuries to as much as 65%.

SUMMARY

Some embodiments of a retractable device can be configured to allow the device to be positioned in an exposed position and a guarded position. For example, the retractable device can include a sheath member having an interior space; a retractable member disposed in the interior space of the sheath member and moveable longitudinally between an exposed position and a guarded position relative to the sheath member; a biasing member disposed longitudinally within the retractable member; and a latch member that locks the retractable member relative to the sheath member in the guarded position. In such circumstances, the latch member can include a release button extending through both the retractable and the sheath members. The retractable member is movable from the exposed position to the guarded position in response to the release button being pushed by a user.

This Summary is an overview of some of the teachings of the present application and not intended to be an exclusive or exhaustive description of the claimed invention. Further details about the present subject matter are found in the detailed description and appended claims. Other aspects of the subject matter will be apparent to persons skilled in the art upon reading and understanding the following detailed description and viewing the drawings that form a part thereof, each of which are not to be taken in a limiting sense. The scope of the claimed invention is defined by the appended claims and their equivalents.

DESCRIPTION OF THE DRAWINGS

The drawings, which are not necessarily drawn to scale, illustrate generally, by way of example, but not by way of limitation, various embodiments discussed in this application.

FIG. 1A is a perspective view of an embodiment of a retractable device in an exposed position.

FIG. 1B is a perspective view of the retractable device illustrated in FIG. 1A in a guarded position.

FIG. 2 is an exploded view of a further embodiment of the retractable device.

FIG. 4A is a perspective view of a latch member of the retractable device of FIG. 2, with the latch member positioned in an extended position.

FIGS. 5A-C are top, side and bottom views of the retractable member of the retractable device illustrated in FIG. 2.

FIGS. 6A-B are perspective views of a support member of the retractable member illustrated in FIGS. 5A-C.

FIG. 6C is a cross sectional view of a locking bridge of the support member illustrated in FIG. 6A along line 6c-6c.

FIG. 6D is a rear end view of the support member illustrated in FIG. 6A.

FIG. 7A is a cross sectional view of the support member illustrated in FIG. 6A.

FIG. 7B is a cross sectional view of the support member illustrated in FIG. 7A with the latch member assembled therein, when the retractable device is in an exposed position.

FIG. 7C is a cross sectional view of the support member illustrated in FIG. 7A with the latch member assembled therein, when the retractable device is in a guarded position.

FIG. 7D is a cross sectional view showing a beveled or tapered edge of the locking bridge of the support member illustrated in FIG. 7A contacting a detent element of the latch member.

FIG. 8A is a perspective view of a sheath member of the retractable device.

FIG. 8B is a cross sectional view of the sheath member of FIG. 8A cooperating with the retractable member and the latch member, when the retractable device is in the exposed position.

FIG. 8C is a cross sectional view of the sheath member of FIG. 8A cooperating with the retractable member and the latch member, when the retractable device is in the guarded position.

FIG. 8D is a side view of a rear end portion of the sheath member showing a compression member.

FIGS. 10A-B are cross sectional views showing an assembling process of the retractable device.

FIGS. 12A-B are perspective views of a still embodiment of a sheath member.

FIGS. 13B-E are perspective views of a support member of the retractable device of FIG. 13A, with a latch member disposed in an interior space of the support member.

FIGS. 14C-F are perspective views of a support member of the retractable device of FIG. 14A, with a latch member disposed in an interior space of the support member.

Like reference symbols in the various drawings indicate like elements.

DETAILED DESCRIPTION

Figure 3A:
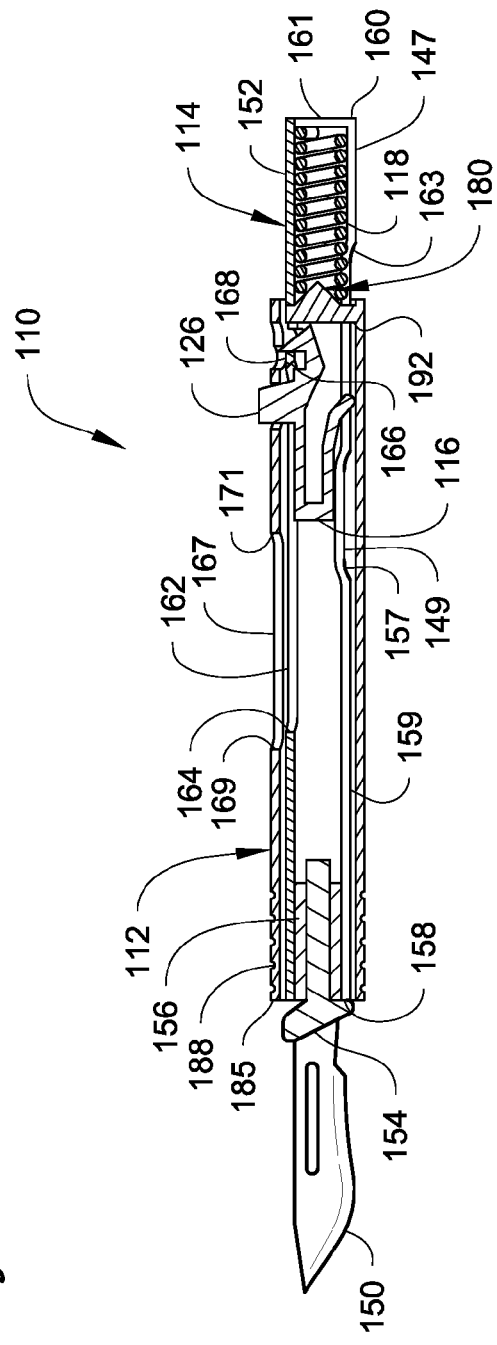
FIG. 3A is a cross sectional view of the retractable device illustrated in FIG. 2, when the device is in an exposed position.

In the following detailed description, reference is made to the accompanying drawings which form a part thereof, and in which is shown by way of illustration specific embodiments in which the inventive concepts may be practiced. These embodiments are described in sufficient detail to enable those skilled in the art to practice the invention, and it is to be understood that the embodiments may be combined or used separately, or that other embodiments may be utilized and that structural and procedural changes may be made without departing from the spirit and scope of the inventive concepts. The following detailed description provides examples, and the scope of the present invention is defined by the claims to be added and their equivalents.

The terms "above," "on," "under," "top," "bottom," "up," "down," "front," "rear," "horizontal," and "vertical" and the like used herein are in reference to the retractable device and the relative positions of its constituent parts, in use when oriented as in the figures.

As used herein, the term "integrally formed" refers to the component being one-piece and/or being formed as a one-piece component, such as a structure having components that are fixedly connected or mounted together in any suitable manner. The term "polyvinylidene fluoride polymer" and acronym "PVDF" refer to the homopolymer, copolymer and terpolymer. It also refers to similar material having an equivalent function. The term "detectable condition" refers to the indication, which may be detected, that tells whether a retractable device is locked in a guarded position. The term "indicia" refer to any mark intended to convey information to the viewer. For example, indicia may include letters, numerals, symbols, characters, designs, pictures, decorations, shapes, geometries, textures, colors or combinations thereof, among other means of relaying information to the viewer.

A retractable device 10 is illustrated as, by way of illustration but not limitation, a retractable surgical knife as shown in FIGS. 1A-B. In some embodiments, the retractable device 10 may include a sheath member 12, a retractable member 14 received telescopically within the sheath member 12, a latch member 16 and a biasing member 18. In such circumstances, the retractable member 14 can be positioned in an exposed position (as shown in FIG. 1A) and a guarded position (as shown in FIG. 1B) relative to the sheath member 12. In some embodiments, when the retractable device 10 is positioned in the exposed position, the length of the retractable device 10 is similar to that of a regular scalpel. This allows the retractable device 10 to have a simple structure and to be cost-effective to assemble, while maintaining a high retraction speed. Moreover, it is intuitive for a user to push a rear end of the retractable member 114 to expose the tool head and push a button on the latch member 16 to retract the retractable member 14. The retractable member 14 can include a tool head 50 and a support member 52, with the tool head 50 being coupled to the support member 52.

It is to be understood that although in the embodiments depicted in the drawings of this disclosure, the sheath member and the retractable member are both depicted as having a circular cross section when they are cut by a plane perpendicular to a longitudinal axis of the sheath member, the cross section of the sheath member and the cross section of the retractable member can have other shapes, such as oval shapes, elliptical shapes, hexagonal shapes, other polygonal shapes, or other shapes. In some embodiments, such as the embodiment shown in FIGS. 1A-B, the shape of the cross section of the retractable member generally tracks the shape of the cross section of the sheath member.

In some embodiments, the length of the retractable device 10 in the exposed position can be similar to that of a non-retractable device. For example, a length of a retractable surgical knife in the exposed position can be similar to that of a non-retractable scalpel.

In some embodiments, most parts of the retractable device 10 can be at least partially made of non-metal materials, such as plastic materials, to allow it to be light so that easier to be manipulated. The lower cost of the materials of the retractable device 10 allows the retractable device 10 to be relatively inexpensive to make, and as a result, allow the device 10 to be disposable. This will further reduce the cost and safety issues for sterilizing the retractable device 10 and changing the tool head 50. Examples of plastic materials may have good mechanical and chemical resistance properties that are retained to high temperatures, such as semi-crystalline thermoplastic materials like Polyether ether ketone (PEEK) and polyvinylidene fluoride polymer (PVDF). These plastic materials can be used to make parts of the retractable device, such as the sheath member 12, the retractable member 14 and the latch member 16.

In some embodiments, the biasing member 18 can be made of metal or metals. However, in some embodiments, the biasing member 18 can also be made of non-metal materials, such as plastic materials, silicon or can be coated with a microfilm (e.g. TEFLON™) or other types of polypropylene materials so that the biasing member 18 is heat/steam resistant and chemical resistant. The tool head 50 can be made of non-metal materials, such as plastic material, and metal or other materials. Accordingly, almost all parts of the retractable device 10 can be injection molded. This can help lower the cost for manufacturing the retractable device 10 more effectively. It is to be understood that in some embodiments, most parts of the retractable device 10 can be made of other materials, such as metal or metals.

In some embodiments, a retractable device 10 can consist essentially of only five integrally formed components: a sheath member 12, a retractable member 14, a latch member 16 and a biasing member 18. In such circumstances, loss of components such as pins, screws, fasteners, links, springs or the like during use or storage of the retractable device can be prevented. This is useful when the retractable device 10 is a retractable surgical knife. In such circumstances because it will help reduce safety issues if loss of components such as pins, screws, fasteners, links, springs or the like in the operative field can be prevented. In addition, fewer components allow easy assembly of the retractable device 10 and as a result allow the cost for manufacturing the device 10 to be lowered more effectively.

Figure 3B:
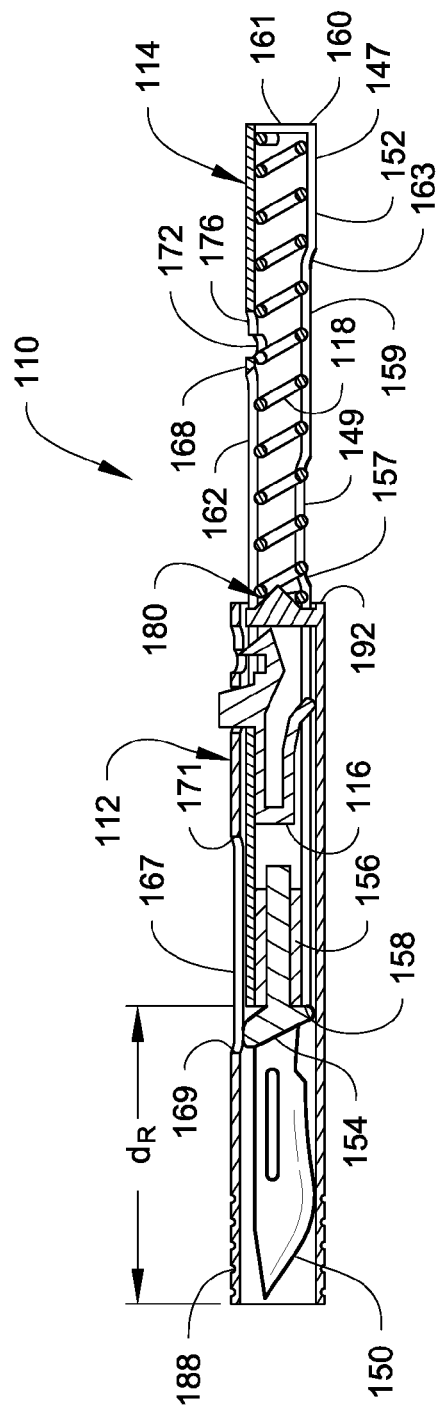
FIG. 3B is a further cross sectional view of the retractable device illustrated in FIG. 2, when the device is in a guarded position.

FIGS. 2 and 3A-B show a particular embodiment of the retractable device 10. As depicted in FIGS. 2 and 3A-B, a retractable device 110 consists essentially of only four integrally formed components sheath member 112, retractable member 114, latch member 116 and a biasing member 118. In such circumstances, loss of components such as pins, screws, fasteners, links, springs or the like during use or storage of the retractable device can be prevented. This is useful when the retractable device 110 is a retractable surgical knife. In such circumstances because it will help reduce safety issues if loss of components such as pins, screws, fasteners, links, springs or the like in the operative field can be prevented.

However, it is to be understood that in other embodiments the retractable device 110 can include more than four integrally formed components. The retractable device 110 has an axial direction X and a radial direction Y. The retractable member 114 can be positioned in an exposed position (as shown in FIG. 3A) and a guarded position (as shown in FIG. 3B) relative to the sheath member 112. Compared to the position in FIG. 3A, the retractable member 114 has retracted a retraction distance $d_R$ in FIG. 3B.

In some embodiments, the length of the retractable device 110 can be about 5.56 inches. The length of the sheath member 112 and the length of the retractable member 114 can be about 71.93 mm, respectively. In other embodiments, the length of the sheath member 112 is longer than the length of the retractable member 114 whereby in one embodiment, retractable member 114 is entirely received in the sheath member 112 when the retractable member 114 is positioned in the exposed position. In some embodiments, the length of the retractable device 110 in the exposed position can be similar to that of a non-retractable device. For example, a length of a retractable surgical knife in the exposed position can be similar to that of a non-retractable scalpel.

Figure 4B:
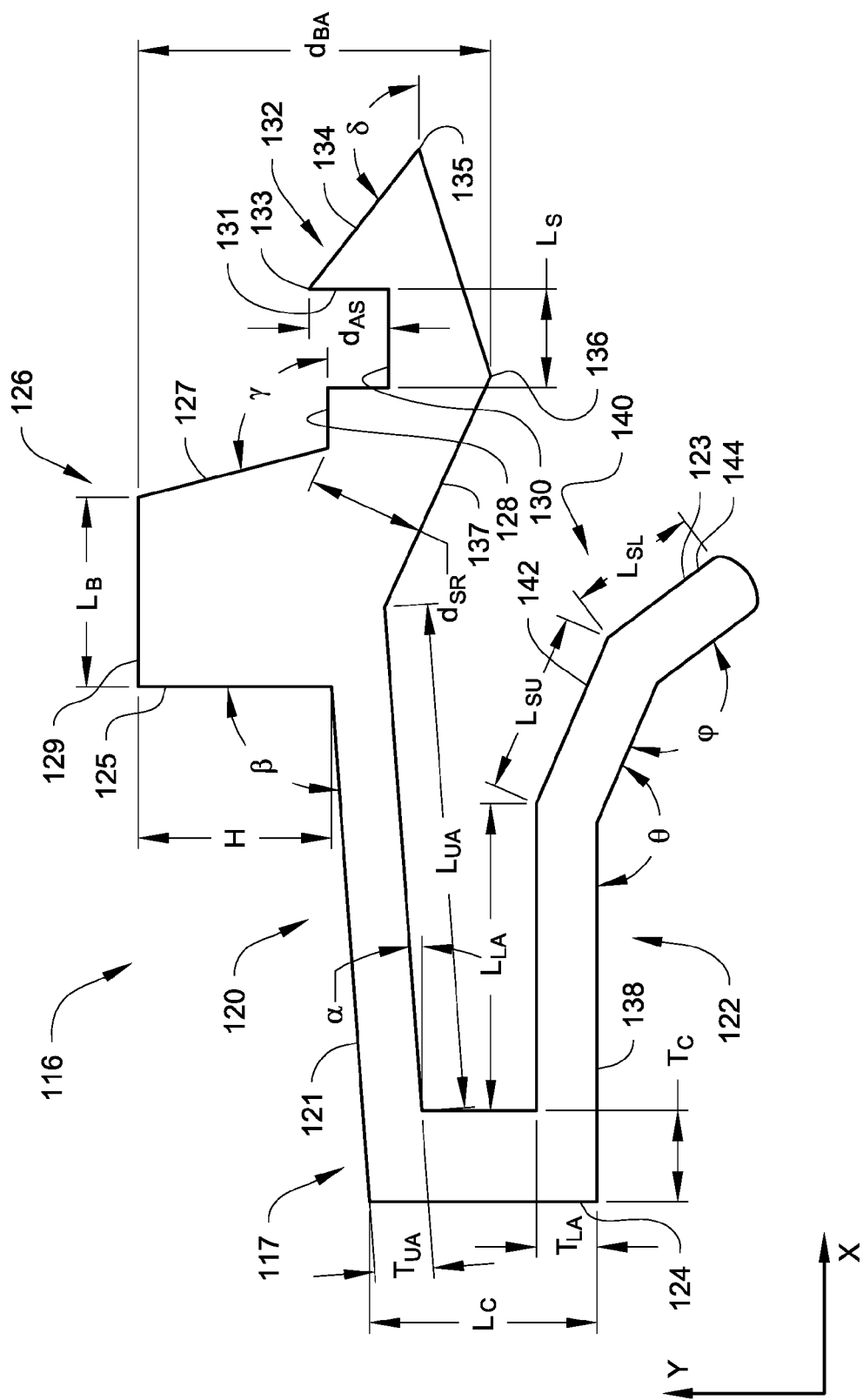
FIG. 4B is a side view of the latch member illustrated in FIG. 4A.
Figure 4C:
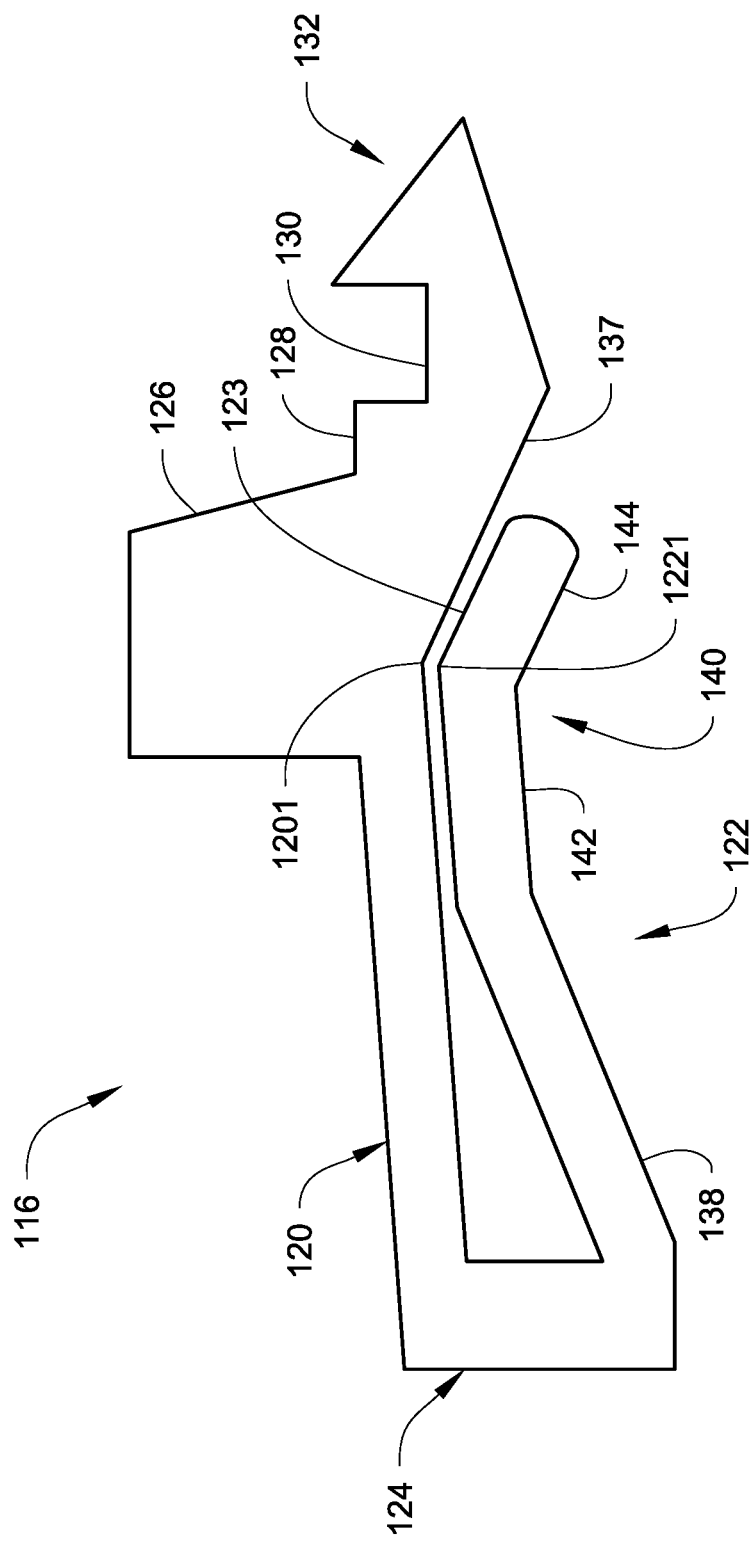
FIG. 4C is a side view of the latch member of FIG. 4A, with the latch member positioned in a fully-compressed position.

Referring to FIGS. 4A-C, in some embodiments, the retractable device includes the latch member 116 to releasably maintain the retractable member 114 when the retractable member is positioned in the guarded position. In such circumstances, the latch member 116 can have a U-shaped latch body 117. As shown in FIGS. 4B-C, the latch member 116 can be positioned in an expanded position (referring to FIG. 4B) and a fully-compressed position (referring to FIG. 4C) with at least a portion of the lower limb 122 being in contact with the upper limb 120. The latch body 117 can be made of suitable material having sufficient resilience and ultimate strength so that it is not easily broken under pressure. For example, the latch body 117 can be made of non-metal materials, such as plastic materials. Examples of plastic materials may have good heat resistance and solvent resistance, high dielectric strength, natural flame resistance, such as ULTEM™ plastics available from Saudi Basic Industries Corporation of Riyadh, Saudi Arabia.

In some embodiments, the latch body 117 can have a resilient upper limb 120, a resilient lower limb 122 and a connecting section 124. For the convenience of description, the left end of the latch body 117 where the connecting section is located is described as a front side and the right end of the latch body 117 is described as a rear side, as they are oriented in an assembled retractable device 110, as shown in FIGS. 4A-C. The connecting section 124 connects the front ends of the upper limb 120 and the lower limb 122, respectively. In some embodiments, the lower limb 122 has an segment extending rearwardly defining an axial direction x of the latch member 116 and the connecting section 124 extending downwardly defining a radial direction y of the latch member 116. When assembled, the axial direction x of the latch member 116 is generally oriented in the same direction as the axial direction X of the retractable device 110, and the radial direction y of the latch member 116 is generally oriented in the same direction as the radial direction Y of the retractable device 110.

Referring to FIG. 4A, in some embodiments, the latch member 116 has a uniform width W. However, it is to be understood that the widths of the upper limb 120, lower limb 122, connecting section 124 and their various components can vary as long as the upper limb 120, lower limb 122, connecting section 124 and their components can cooperate properly with openings or slots defined in the sheath member 112 and retractable member 114 during the process of assembly or use.

As depicted in FIGS. 4A-C, in some embodiments, the upper limb 120 includes an elongated aim segment 121 extending axially and slightly upwardly relative to the axial direction x. The arm segment 121 has a length $L_{UA}$ and a thickness $T_{UA}$. The arm segment 121 has an upper surface and a lower surface generally parallel to each other. An angle α is defined between the arm segment 121 and the axial direction x.

In some embodiments, the upper limb 120 can further include a release button 126 configured to release a latch between the sheath member 112 and the retractable member 114, thereby allowing the retractable member 114 to retract from the exposed position. In such circumstances, the release button 126 can protrude beyond the outer surface of the sheath member 112. As a result, the release button 126 can help prevent the retractable device 110 from rolling more than 180 degrees on a flat of slightly inclined surface.

The release button 126 can extend upwardly from an upper surface of the arm segment 121, with a front surface 125 of the release button 126 extending upwardly in a generally radial direction y from the upper surface of the arm segment 121. The front surface 125 has a height H. An angle β is formed between the front surface 125 of the release button 126 and the upper surface of the arm segment 121.

In some embodiments, the release button 126 may include a top surface 129 having a length $L_B$ and an inclined button ramp 127 configured to allow a low friction contact to be formed when the release button 126 is pressed downwardly to release the latch between the sheath member 112 and retractable member 114.

The button ramp 127 can extend from a rear edge of an upper surface of the release button 126 downwardly and rearwardly. A positioning step 128 extends from a lower edge of the button ramp 127 rearwardly in generally the axial direction x of the latch member 116. In such circumstances, the positioning step 128 can help limit the release button 126 from traveling upwardly beyond a top wall of the retractable member 114. As a result, the positioning step 128 defines a radial position of the latch member 116 relative to the sheath member 112, and in turn defines a radial position of the latch member 116 relative to the retractable member 114. In such circumstances, the positioning step 128 can help locate a detent ramp 134 of the latch member 116 for a successful locking action.

As shown in FIGS. 4A-C, an angle γ can be formed between the button ramp 127 and the positioning step 128. In such circumstances, the upper limb 120 can include a detent element 132 located at a rear portion of the upper limb 120. The detent element 132 is configured to allow the upper limb 120 to be deflected downwardly, thereby allowing a portion of the retractable member 114 to pass through the detent element 132 and be received in a locking slot 130 formed between the detent element 132 and the positioning step 128, when the retractable device 110 is assembled. As a result, the retractable member 114 can be latched to the sheath member 112, allowing the retractable member 114 to be maintained in the exposed position. The locking slot 130 can have a length $L_S$ defined between the positioning step 128 and a front surface 131 (referring to FIG. 4B) of the detent element 132.

In some embodiments, the detent element 132 can extend upwardly from the locking slot 130 to a detent apex 133 and then angles rearwardly and downwardly toward a rear end 135 of the upper limb 120. As shown in FIGS. 4A-C, the detent apex 133 is located at a distance $d_{AS}$ from a lower surface of the positioning step 128. The detent ramp 134 can be defined between the detent apex 133 and the rear end 135. The detent ramp 134 can be configured to deflect the upper limb 120 rapidly and smoothly and thereby allows the retractable member 114 to be latched with the sheath member 112 effectively.

As shown in FIGS. 4A-C, an angle δ can be formed between the detent ramp 134 and the axial direction x. In some embodiments, the upper limb 120 can include a latch positioning apex 136 located on a lower surface of the upper limb 120. The latch positioning apex 136 can be located generally below the positioning step 128. However, it is to be understood that the latch positioning apex 136 can be located at other locations on the lower surface of the upper limb 120. The latch positioning apex 136 can be located at a distance $d_{BA}$ from the top surface 129 of the release button 126.

Still referring to FIGS. 4A-C, a lower limb nesting ramp 137 can be formed at a lower surface of the upper limb 120 on a rear side of the latch positioning apex 136 to allow a front portion of the lower limb 122 to nest thereupon, when the lower limb 122 is compressed to the upper limb 120. A lower edge of the button ramp 127 is located at a distance $d_{SR}$ from the lower limb nesting ramp 137. An arm segment 138 of the lower limb 122 has a length $L_{LA}$ and a thickness $T_{LA}$ and the connecting section 124 has a length $L_C$ and a thickness $T_C$.

In some embodiments, the distance $d_{BA}$ is configured to be no greater than an inner diameter of the sheath member 112. However, it is to be understood, in other embodiments, a lowest end 196 of the lower limb 122 is positioned vertically further away from the top surface 129 of the release button 126 than the latch positioning apex 136, when the latch is in a fully-compressed position. This configuration allows the latch member 116 to slide easily to its position during an assembling process.

In some embodiments, the thickness $T_{UA}$ of the upper limb 120 and the thickness $T_{LA}$ of the lower limb 122 can be generally equal to each other, and the thickness $T_C$ of the connecting section 124 is greater than the thickness $T_{UA}$ of the upper limb 120 or the thickness $T_{LA}$ of lower limb 122, thereby allowing an adequate elastic force to be produced for actuate the latch member 116. However, it is to be understood that in other embodiments, the thickness $T_{UA}$ of the upper limb 120 and the thickness $T_{LA}$ of the lower limb 122 can be different from each other.

In some embodiments, the lower limb 122 can have the arm segment 138 and a balancing element 140. The balancing element 140 has an upper portion 142 and a lower portion 144. The upper portion 142 has a length $L_{BU}$ and the lower portion 144 has a length $L_{BL}$.

As shown in FIGS. 4A-C, an angle θ is formed between the arm segment 138 and the upper portion 142, and an angle φ is formed between the upper portion 142 and the lower portion 144. The lower limb 122 is configured to allow at least a portion of the balancing element 140 to extend outside the retractable member 114 when installed in the retractable member 114 to balance the movement of the retractable member 114 relative to the sheath member 112.

In addition, the lower limb 122 is configured to allow an upper surface 123 of the lower portion 144 of the balancing element 140 to nest upon the lower limb nesting ramp 137, which is formed on the lower surface of the upper limb 120. In some embodiments, when the latch member 116 is positioned in the fully-compressed position, the entire upper surface 123 of the lower portion 144 of the balancing element 140 rests on the lower limb nesting ramp 137. In some embodiments, when the latch member 116 is positioned in the fully-compressed position, at least a portion of the upper surface 123 of the lower portion 144 of the balancing element 140 rests on the lower limb nesting ramp 137. In some embodiments, when the latch member 116 is positioned in the fully-compressed position, a convex point 1221 formed between the upper portion 142 and the lower portion 144 of the balancing element 140 nests at a concave point 1201 formed between the lower limb nesting ramp 137 and the arm segment 121 of the upper limb 120.

In the embodiment depicted in FIGS. 4A-C, rigid transitions are formed between the arm segment 138 and the upper portion 142, and between the upper portion 142 and the lower portion 144. In other embodiments, a smooth transition, such as a smooth curved transition, can be Ruined between these portions.

In some particular embodiments, the length $L_{UA}$ of the arm segment 121 of the upper limb 120 can be about 0.40 inches, the angle α defined between the arm segment 121 and the axial direction x can be about 5°, the height H of the front surface 125 of the release button 126 can be about 0.16 inches. In such circumstances, the angle β, which is formed between the front surface 125 of the release button 126 and the upper surface of the arm segment 121, can be about 95°, thereby aiding in an unimpeded retraction of the retractable device 110. Specifically, when the retractable device 110 is in use, the angle β, when being slightly greater than 90°, allows a front end 197 of the upper limb 120 to be positioned slightly away from an inner surface of the sheath member 112 to form a gap 199, thereby allowing a top wall portion 198 of the retractable member 114 to pass through the gap 199 between the upper limb 120 and the inner surface of the sheath member 112 (referring to FIG. 3A). As a result, the top wall portion 198 of the retractable member 114 can travel continually to its resting position against the front surface 125 of the release button 126.

In these particular embodiments, the length $L_B$ of the top surface 129 of the release button 126 can be about 0.15 inches, the angle γ formed between the button ramp 127 and the positioning step 128 can be about 102°, the length $L_S$ of the locking slot 130 can be about 0.08 inches, the distance $d_{AS}$ between the detent apex 133 and the lower surface of the positioning step 128, can be about 0.07 inches, the angle δ formed between the detent ramp 134 and the axial direction x can be about 140°, the distance $d_{BA}$ between the latch positioning apex 136 and the top surface 129 of the release button 126 can be about 0.30 inches, the distance $d_{SR}$ between the lower edge of the button ramp 127 and the lower limb nesting ramp 137 can be about 0.09 inches, the length $L_{LA}$ of the arm segment 138 of the lower limb 122 can be about 0.24 inches, the length $L_C$ of the connecting section 124 can be about 0.19 inches, the thickness $T_{LA}$ of the arm segment 138 of the lower limb 122 can be about 0.05 inches, the length $L_{BU}$ of the upper portion 142 of the balancing element 140 can be about 0.15 inches, the length $L_{BL}$ of the lower portion of the balancing element 140 can be about 0.10 inches, the angle θ formed between the arm segment 138 and the upper portion 142 can be about 157°, and the angle φ formed between the upper portion 142 and the lower portion 144 can be about 148°.

Referring to FIGS. 5A-C, in some embodiments, the retractable member 114 has a support member 152 and a tool head 150 mounted on a front end 158 of the support member 152. In such circumstance, the tool head 150 can be configured to be retracted entirely into the sheath member 112, and thereby shielded entirely in the sheath member 112.

However, it is to be understood that in other embodiments, the tool head 150 does not have to be retracted entirely into the sheath member 112 so long as the tool head 150 is safeguarded from injuring the user.

In some embodiments, the tool head 150 is a blade having a cutting edge 153 and a front point 155. The front point 155 can be rounded, as typical for standard #10 blades. In addition, the front point 155 can be pointed, as found in standard #11 blades, or like a hook, as found in standard #12 blades. The blades can also be small tip blades, as found in standard #15 blades, or bigger blades, as founded in standard #20 blades. In some embodiments, the tool head 150 of the retractable device 110 can be any type of scalpel blades, i.e., the retractable device 110 can be employed with any scalpel blade configuration.

In some embodiments, the retractable member 114 can be formed by securely attaching the tool head 150 to the support member 152 by a tool head retention element 154 and a coupling element 156. As shown in FIGS. 5A-C, the tool head retention element 154 can be configured to be secured to the tool head 150 at its front end and to the coupling element 156 at its rear end. In such circumstances, the tool head retention element 154 can have a front portion to which the tool head 150 is secured and a rear portion receivable in a bore of the coupling element 156. The coupling element 156 can have a cylindrical body receivable in a front end of the support member 152. The coupling element 156 is in turn secured to a front end 158 of the support member 152.

The tool head retention element 154 and the coupling element 156 can be standard and universal which are able to receive most regular tool heads, such as regular scalpel blades.

It is to be understood that, in some embodiment, the tool head 150 is attached to the support member 152 by the tool head retention element 154 and the coupling element 156 to form an inseparable structural member by fastening means such as solder, adhesive, or the like. In other embodiments, the tool head 150 can be removably attached to the support member 152 by the tool head retention element 154 and the coupling element 156, or other coupling mechanisms. It is to be understood that various mechanisms can be used for attaching the tool head 150 to the support member 152.

FIGS. 6A-B illustrate perspective views of the support member 152 of the retractable member 114. FIG. 6C illustrates a cross-sectional view of a locking bridge of the support member 152 of FIG. 6A along line 6c-6c. FIG. 6D illustrates a rear end view of the support member 152. FIGS. 7A-C illustrate cross sectional views of the support member 152. FIG. 7A illustrates the support member 152 without the latch member 116 being assembled therein. FIG. 7B illustrates the support member 152 with the latch member 116 being assembled in the exposed position. FIG. 7C illustrates the support member 152 with the latch member 116 being assembled in the guarded position.

As shown in FIGS. 6A-B and 7A-C, the support member 152 has an elongated body having the front end 158 and a rear end 160, with a rear wall 161 located at the rear end 160. Referring to FIGS. 6A-B and 7A-C, in some embodiments, the support member 152 can have an upper limb bypass slot 162 defined at a top side of the support member 152. The upper limb bypass slot 162 can have a front end 164, a rear end 166 and two parallel edges extending in an axial direction between the front and rear ends 164, 166.

As shown in FIGS. 7B-C, the width defined between the parallel edges of the upper limb bypass slot 162 can be slightly greater than the width W of the upper limb 120 of the latch member 116, thereby when the latch member 116 is assembled in the support element 152, the width of the upper limb bypass slot 162 allows the upper limb bypass slot 162 to slide snugly past the upper limb 120 of the latch member 116. However, it is to be understood that the width of the upper limb bypass slot 162 can be much larger than the width of the upper limb 120, as desired.

As shown in FIGS. 3A-B and 7A-C, in some embodiments, the front end 164 and rear end 166 of the upper limb bypass slot 162 define a retraction stop and a projection stop for the latch member 116, respectively. As shown in FIGS. 3A and 7B, when the retractable member 114 is in the exposed position, the release button 126 of the latch member 116 is positioned in a vicinity of the rear end 166 of the upper limb bypass slot 162. As used in the embodiment depicted in FIGS. 3A-B and 7A-C, the term "vicinity" means a distance ranging from about 0.10 inches to about 0.60 inches, such as about 0.20 inches.

As shown in FIGS. 3B and 7C, when the retractable member 114 is in the guarded position, the release button 126 of the latch member 116 is positioned to abut the front end 164 of the upper limb bypass slot 162. In such circumstances, the length of the upper limb bypass slot 162 determines the retraction distance $d_R$ (shown in FIG. 3B). For tool heads 150 having different lengths, the length and position of the upper limb bypass slot 162 can vary to allow appropriate tool head deployment and retraction. That is, the length and position of the upper limb bypass slot 162 can be configured to allow a suitable portion of the retractable member 114, for example, the entire tool head 150, to be exposed in the exposed position, and to allow the retractable member 114, for example, the tool head 150, to be appropriately guarded within the sheath member 112. The position of the upper limb bypass slot 162 relative to the front end 158 of the retractable member 114 allows use with blades of different lengths.

In some embodiments, the retraction distance $d_R$ may range from about 0.5 inches to about 3.5 inches. In one example, the retraction distance $d_R$ can be about 2 inches.

Referring to FIGS. 6A, 6C and 7A-C, the support member 152 includes a locking bridge 168 defining the rear end 166 on its front edge 170 and defining at least a portion of the front edge of a detent apex receiving opening 172 on its rear edge 174. As shown in FIGS. 3A and 7B, in use, when the retractable member 114 moves to the exposed position, the locking bridge 168 slides on the detent ramp 134 of the detent element 132 of the latch member 116, thereby deflecting the upper limb 120 of the latch member 116 downwardly toward a bottom side of the retractable member 114. After the rear edge 174 of the locking bridge 168 passes the detent apex 133 of the detent element 132, the locking bridge 168 is received by the locking slot 130 of the latch member 116 and engaged with the latch member 116, with the rear edge 174 of the locking bridge 168 abutting the front surface 131 of the detent element 132 of the latch member 116. In such circumstances, the locking bridge 168 of the retractable member 114 is captured or locked in the locking slot 130 of the latch member 116, and the detent element 132 of the latch member 116 is received in the detent apex receiving opening 172.

In some embodiments, the detent apex receiving opening 172 can have a larger width compared to the width W of the upper limb 120 of the latch member 116 to avoid the detent element 132 of the latch member 116 contacting side edges of the detent apex receiving opening 172, thereby avoiding friction produced by the contact. In addition, the larger width of the detent apex receiving opening 172 allows the front surface 131 of the detent element 132 of the latch member 116 to be in contact with the front edge of the detent apex receiving opening 172 entirely. As shown in FIG. 6A, in some embodiments, the width of the detent apex receiving opening 172 is greater than the width of the upper limb bypass slot 162.

Referring to FIG. 6C, in some embodiments, the locking bridge 168 is beveled or tapered when extending from the rear edge 174 toward the front edge 170. In some embodiments, the locking bridge 168 has a uniform thickness and only the front edge 170 is beveled or tapered. The beveled or tapered front edge 170 of the locking bridge 168 and the detent ramp 134 of the detent element 132 of the latch member 116 cooperate to allow a friction produced during the latching process, such as a friction produced by the movement of the locking bridge 168 over the detent ramp 134 of the detent element 132 of the latch member 116 to be reduced. In some embodiments, the tapered edge has an angle τ ranging from about 10° to about 80°. In one example, the angle τ can be about 30°

As shown in FIGS. 6A and 7A-C, the rear end of the detent apex receiving opening 172 is connected with a detent travel opening 176. The detent travel opening 176 is configured to allow the detent element 132 of the latch member 116 to travel rearwardly. In such circumstances, the detent travel opening 176 is configured to have a length $L_{DT}$ (referring to FIG. 6A) that is long enough to allow the entire detent element 132 of the latch member 116 to pass through the lower side of the locking bridge 168 of the support member 152 until the upper limb 120 of the latch member 116 flexes back by the resilience of the latch member 116 and the detent element 132 engages with the rear edge 174 of the locking bridge 168 at its front surface 131.

Referring to FIG. 6A, in some embodiments, the detent travel opening 176 can have a smaller width than the width of the detent apex receiving opening 172. For example, the width of the detent travel opening 176 can be generally the same as the width of the upper limb bypass slot 162, which is slightly greater than the width W of the upper limb 120 of the latch member 116. However, it is to be understood that in some embodiments, the width of the detent travel opening 176 can be larger than the width of the upper limb bypass slot 162.

Referring to FIGS. 6B, 6D, and 7A-C, in some embodiments, the support member 152 has a compression member bypass slot 146 at a bottom side of the support member 152 extending from the front end 158 to the rear end 160, cutting through the rear wall 161 located at the rear end 160 of the support member 152. The compression member bypass slot 146 includes a bottom wall slot 147 at a bottom side of the support member 152 and a rear wall slot 148 defined in the rear wall 161 that allow the bottom wall and the rear wall 161 to bypass a compression member 180 located on the sheath member 112.

Still referring to FIGS. 6B and 7A-C, the bottom wall slot 147 has a pair of parallel edges extending axially between the front end 158 and the rear end 160 of the support member 152. A width of the bottom wall slot 147 is defined between the two parallel edges. The shape of the rear wall slot 148 can be determined by the shape of the compression member 180 located on the sheath member 112 (described in more detail below in connection with FIGS. 8A-D).

Referring to FIGS. 6B and 7A-C, in some embodiments, the bottom wall slot 147 can include a lower limb bypass slot 159 for the lower limb 122 of the latch member 116 to pass through. In such circumstances, the lower limb bypass slot 159 works with the upper limb bypass slot 162 to allow the latch member 116 to slide between the guarded position and the exposed position relative to the retractable member 114.

In the depicted embodiment, the rear end 163 of the lower limb bypass slot 159 can be located generally below the locking bridge 168 or at a rear side of the locking bridge 168 (also comparing between FIGS. 6A-B), allowing the latch member 116 to travel rearwardly until the detent element 132 is engaged with the locking bridge 168. It is to be understood that although in the embodiment depicted in FIGS. 6A-B and 7A-C, the lower limb bypass slot 159 does not have a front end, the lower limb bypass slot 159 can in fact include a front end located at a front side of the front end 164 of the upper limb bypass slot 162.

In some embodiments, the lower limb bypass slot 159 can have a length ranging from about 2 inches to about 4 inches. In one example, the length of the lower limb bypass slot 159 can be about 3 inches.

Still referring to FIGS. 6B and 7A-C, in some embodiments, the lower limb bypass slot 159 can include a biasing member introduction slot 149 for introduction of the biasing member 118. In the depicted embodiment, a front end 157 of the biasing member introduction slot 149 is located at a rear side of the front end 164 of the upper limb bypass slot 162 (also comparing between FIGS. 6A-B). It is to be understood that the biasing member introduction slot 149 can be located at various locations along the bottom wall slot 147.

In some embodiments, the biasing member introduction slot 149 can have a length ranging from about 0.30 inches to about 2.50 inches. In one example, the length of the biasing member introduction slot 149 can be about 0.80 inches. In some embodiments, the length of the biasing member introduction slot 149 is configured to be as small as possible to decrease the chance of disfigurement of the biasing member 118 during compression, as long as the length of the biasing member introduction slot 149 is great enough for introduction of the biasing member 118. This can help reduce uneven compression of the biasing member 118.

It is to be understood that the biasing member introduction slot 149 can be located at various locations along the length of the bottom wall slot 147 as long as when the retractable member 114 is in the guarded position, at least a portion of the biasing member introduction slot 149 can be exposed outside the sheath member 112 for assembling the biasing member 118 in the retractable member 114.

In some embodiments, in the exposed position, the biasing member introduction slot 149 is completely covered by the sheath member 112. In other embodiments, as shown in FIG. 3B, in the guarded position, the biasing member introduction slot 149 is completely exposed outside the sheath member 112 for easy introduction of the biasing member 118.

Referring to FIG. 6B, in some embodiments, the bottom wall slot 147 may have different width defined between its parallel edges. In the depicted embodiments, a smallest width of the bottom wall slot 147 can be as small as slightly greater than the thickness of a lower end 192 of the compression member 180 (referring to FIG. 3), which connects the compression member 180 to an inner surface of the sheath member 112, thereby allowing the bottom wall slot 147 to slide past the compression member 180 of the sheath member 112. The section of the lower limb bypass slot 159 of the bottom wall slot 147 can have a larger width which is slightly greater than the width W of the lower limb 122 of the latch member 116, allowing the lower limb bypass slot 159 to slide snugly past the lower limb 122 of the latch member 116. The section of the biasing member introduction slot 149 of the lower limb bypass slot 159 can have the largest width which is the same as, or slightly smaller than, the diameter of the biasing member 118, which allows introduction of the biasing member 118. However, it is to be understood that the relative sizes of different sections of the bottom wall slot 147 can vary. For example, in some embodiments, the width of the section of the lower limb bypass slot 159 can be the smallest among the different sections. In some embodiments, the different sections of the bottom wall slot 147 can have a uniform width.

Referring to FIGS. 6B and 7A-C, in some embodiments, a rear end 165 of the biasing member introduction slot 149 is located at a front side of the rear end 163 of the lower limb bypass slot 159. However, the locations of the biasing member introduction slot 149 relative to the lower limb bypass slot 159 can vary (described in more detail below in connection with FIG. 10).

The dimension of the rear wall slot 148 of the compression member bypass slot 146 can vary as long as the rear wall slot 148 can slide past the compression member 180 located on the sheath member 112 (described in more detail below in connection with FIGS. 8A-D). In the embodiment depicted in FIGS. 6A-B and 6D, the dimension of the rear wall slot 148 of the compression member bypass slot 146 is slightly greater than the dimension of the compression member 180 located on the sheath member 112, thereby allowing the rear wall slot 148 to slide past the compression member 180.

Referring now to FIGS. 8A-C, in some embodiments, the sheath member 112 has an elongated body having a front end 185 of the sheath member 112, a rear end 189 of the sheath member 112 and a length defined between the front end 185 of the sheath member 112 and the rear end 189 of the sheath member 112. In some embodiments, the sheath member 112 includes a latch introduction slot 167 defined at a top side of the sheath member 112. The latch introduction slot 167 has a front end 169, a rear end 171 and a length defined between the front end 169 and the rear end 171. In some embodiments, the length of the latch introduction slot 167 is greater than the entire length of the latch member 116 (referring to FIGS. 3A-B).

Referring to FIG. 8B, when the retractable member 114 is in the exposed position, the latch introduction slot 167 of the sheath member 112 can be located in a location such that at least a portion of the latch introduction slot 167 is overlapped with the upper limb bypass slot 162 of the retractable member 114. In such circumstances, the rear end 171 of the latch introduction slot 167 can be positioned at a front side of the rear end 166 of the upper limb bypass slot 162. The overlap of the latch introduction slot 167 and the upper limb bypass slot 162 allows the latch member 116 to be inserted in the retractable member 114 through these slots. In some embodiments, the front end 169 of the latch introduction slot 167 is located on a rear side of the front end 164 of the upper limb bypass slot 162 (referring to FIG. 3A), thereby providing an opening passing through the entire latch introduction slot 167 and the upper limb bypass slot 162. As a result, the latch introduction slot 167 of the sheath member 112 and the upper limb bypass slot 162 of the retractable member 114 can be positioned to allow a longer overlapped opening section for a more convenient insertion of the latch member 116.

As shown in FIG. 8A, the latch introduction slot 167 can have a width that is generally the same as the width of the upper limb bypass slot 162, which is slightly greater than the width W of the upper limb 120 of the latch member 116. However, it is to be understood that in some embodiments, the width of the latch introduction slot 167 can be greater or smaller than the width of the upper limb bypass slot 162, as long as the width of the latch introduction slot 167 is greater than the width of the upper limb 120 of the latch member 116.

Referring to FIGS. 8A-C, in some embodiments, the sheath member 112 may include a latch button slot 173 located on the rear side of the latch introduction slot 167. The latch button slot 173 can be configured to allow the release button 126 of the latch member 116 to protrude therethrough, thereby maintaining the release button 126, and the latch member 116 in turn, in a relatively fixed position to the sheath member 112.

The latch button slot 173 can have a length and a width that are slightly greater than those of the release button 126, respectively, thereby allowing the release button 126 of the latch member 116 to be received in the latch button slot 173 snugly. However, it is to be understood that in some embodiments, the length and width of the latch button slot 173 can be much greater than those of the release button 126, as desired.

Referring to FIGS. 8A-C, the rear end of the latch button slot 173 is defined by a front edge 175 of a positioning bridge 177. In some embodiments, the front edge 175 of the positioning bridge 177 can be configured to have a greater width relative to a front portion of the latch button slot 173. In such instances, the relatively wide front edge 175 of the positioning bridge 177 provides a flat edge that can cooperate with the inclined button ramp 127 of the release button 126 of the latch member 116, while avoiding the friction occurring between the release button 126 of the latch member 116 and the left and right edges of the latch button slot 173. When the retractable device 110 is in the exposed position as shown in FIG. 8B, the front edge 175 of the positioning bridge 177 is positioned to abut the inclined button ramp 127 of the release button 126 of the latch member 116.

As shown in FIGS. 8A-C, in some embodiments, the positioning bridge 177 is configured to be engaged with a top surface of the positioning step 128 of the latch member 116, at least when the retractable member 114 is not in the exposed position (referring to FIG. 8C). This helps limit the upper limb 120 of the latch member 116 from moving upwardly. In such instances, the positioning bridge 177 helps limit the upward movement of the detent element 132, thereby allowing the locking bridge 168 to slide on the detent ramp 134 of the latch member 116 smoothly, right before the detent element 132 engages with the locking bridge 168 and the retractable member 114 moves into the exposed position.

Referring to FIGS. 8A-C, in some embodiments, a sheath detent opening 179 can be formed on a rear side of the positioning bridge 177 to allow a full upward movement of the detent element 132 of the latch member 116. This can help ensure a firm locking between the detent element 132 and the locking bridge 168. In the embodiment depicted in FIGS. 8A-C, the sheath detent opening 179 can have a contour that generally tracks the entire contour of the detent apex receiving opening 172 and the detent travel opening 176 defined in the retractable member 114. In some embodiments, the length of the sheath detent opening 179 can be shorter than the total length of the detent apex receiving opening 172 and the detent travel opening 176. However, it is to be understood that the shape of the sheath detent opening 179 can vary as long as the opening is large enough to allow a full upward movement of the detent element 132 of the latch member 116.

Referring to FIGS. 8A-D, in some embodiments, the sheath member 112 can have the compression member 180 as mentioned above extending rearwardly for compressing and in some embodiments centralizing the biasing member 118. In such circumstances, the compression member 180 can be integrally formed on the inner surface of the sheath member 112 at its lower end 192. However, it is to be understood that the compression member 180 can also be fabricated separately and attached to the inner surface of the sheath member 112 at its lower end 192. In some embodiments, the largest diameter $d_{CE}$ of the compression member 180 is configured to allow the compression member 180 to be engageable with the biasing member 118.

Referring to FIGS. 9A-D, in some embodiments, when the biasing member 118 takes the form of a spring, the compression member 180 can have a tapered shape for even compression of the biasing member 118 during the compression process. In such circumstances, the compression member 180 can help reduce the friction occurred between the biasing member 118 and the inner wall surface of the retractable member 114, and help avoid deformation such as bulging of the biasing member 118.

Still referring to FIGS. 9A-D, in some embodiments, the compression member 180 can have a symmetrically-tapered shape to help further reduce the friction occurred between the biasing member 118 and the inner wall surface of the retractable member 114, and help further avoid deformation such as bulging of the biasing member 118. The symmetrically-tapered shape can be a cone shape, a pyramid shape, an arrow shape, or the like. The compression member 180 is axially oriented in the sheath member 112, with its axis substantially overlapping with the longitudinal axis of the sheath member 112.

The symmetrically-tapered compression member can have various configurations. In the embodiment depicted in FIGS. 8A-D and 9A, the compression member 180 includes a tapered structure, e.g., an arrow-shaped plate, for engagement with a front end 139 of the biasing member 118. The symmetrically-tapered sides 187 of the compression member 180 can help evenly distribute the force at least partially over the inner periphery of the front end 139 of the biasing member 118. As a result, the symmetrically-tapered sides help keep the biasing member 118 centered on the compression member 180, when the biasing member 118 pass around the tapered sides.

Figure 9A:
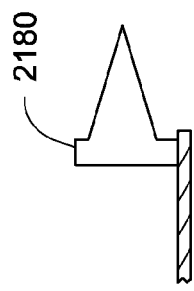
FIG. 9A is a sectional view of a compression member of the sheath member of FIGS. 8A-D.
Figure 9C:
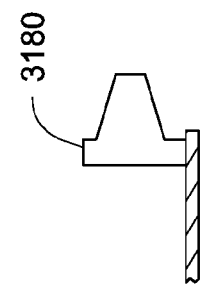
FIGS. 9B-D are sectional views of alternative embodiments of the compression member.
Figure 9B:
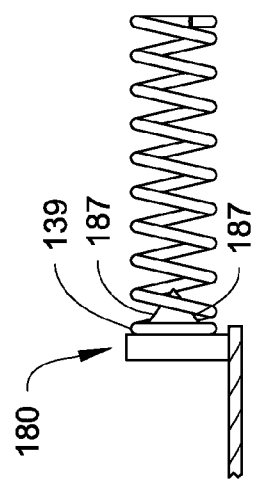
Figure 9D:
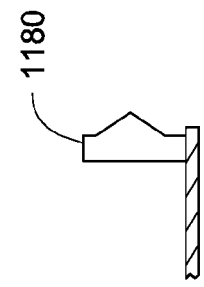

FIG. 9B shows a compression member 1180 that extends less rearwardly than the compression member 180 in FIGS. 8A-D and 9A. FIG. 9C shows a compression member 2180 that extends more rearwardly than the compression member 180 in FIGS. 8A-D and 9A. FIG. 9D shows a compression member 3180 that does not have a sharp rear end, for example, having a trapezoidal shape. It is to be understood that the compression member can have a non-tapered shape, such as a cylindrical shape, or the like, as long as it is engageable with the biasing member 118.

In the embodiment depicted in FIGS. 8A-C and 9A, the compression member 180 can have an engagement mechanism 184 for engaging with a front end 139 of the biasing member 118. In some examples, when the biasing member 118 takes the form of a spring, the engagement mechanism 184 can include an upper flange and a lower flange formed at the two opposite edges of the tapered structure along the largest diameter $d_{CE}$ of the compression member 180. In such circumstances, the upper and lower flanges not only allow front end 139 of the biasing member 118 to be seated on the flanges, but also help achieving even compression of the biasing member. As a result, friction between the biasing member 118 and the inner surface of the support member 152 can be minimized.

In some embodiments, the diameter of the base portion of the tapered structure can be slightly smaller than the diameter of the biasing member 118, thereby allowing the end of the biasing member 118 to engage with the engagement mechanism 184, for example, the upper and lower flanges, of the compression member 180. In the embodiments when the compression member 180 includes a central pyramidal element, the engagement mechanism 184 can be a flange extending radially outwardly from the central pyramidal element for engagement with the biasing member 118.

In some embodiments, a gap 190 can be formed between the compression member 180 and the inner surface of the sheath member 112 for allowing the locking bridge 168 to pass the compression member 180 and slide on the detent ramp 134 of the latch member 116. This can gap allows a wall of the retractable member 114 to pass through the entire length of the sheath member 112. The size of the gap 190 can be slightly greater than the thickness of the side wall of the retractable member 114. In some embodiments, the size of the gap 190 may range from about 0.01 inches to about 0.10 inches. In one example, the gap 190 can be about 0.05 inches. The dimension of the rear wall slot 148 formed on the retractable member 114 is configured to slide past the compression member 180 to allow easy assembly.

Referring to FIG. 8A, an outer surface of the sheath member 112 may include surface roughening 188 toward its front end, such as friction grooves, so that the user can easily grab or control the retractable device 110 during use. The surface roughening 188 can help prevent slippage of user's fingers during use of the retractable device 110. It is to be understood that the type and location of the surface roughening can vary as long as it can help prevent slippage of user's fingers.

Referring back to FIGS. 2 and 3A-B, the retractable device 110 may include the biasing member 118, such as, but not by way of limitation, a spring, elastic, resilient, or compressible element or material. In such circumstances, the biasing member 118 can be disposed on a rear side of both the tool head 150 and the latch member 116. This allows a long retraction distance $d_R$ (shown in FIG. 3B) without having to move the latch member 116 relative to the sheath member 112. However, it is to be understood that the biasing member 118 can be positioned between the tool head 150 and the latch member 116 or at other locations.

In some embodiments, the basing member 118 can be disposed between the rear end 160 of the support member 152 and a rear portion of the sheath member 112. In such circumstances, the biasing member 118 can configured to bias against an engagement portion of the sheath member 112, e.g., a surface of the compression member 180. When in use, the biasing member 118 is compressed or released between the compression member 180 of the sheath member 112 and the rear end 160 of the support member 152 when the retractable member 114 is slidably moved relative to the sheath member 112.

In some embodiments, the biasing member 118 takes the form of a spring. In such circumstances, when in the exposed position, the biasing member 118 is compressed to a fraction of its more relaxed length, thus allowing a lengthy blade excursion. For example, as shown in FIGS. 3A-B, in some embodiments, a length of the compressed biasing member 118 (referring to FIG. 3A) is no more than ½ of the length of the more relaxed length of the biasing member 118 (referring to FIG. 3B).

In some embodiments, the biasing member 118 can be configured to cause the retractable member 114 to retract rapidly once the retractable member 114 is released from the engagement with the detent element 132 of the latch member 116. In such circumstances, the biasing member 118, such as a spring, can have a sufficiently great compression constant such that the biasing member 118 can cause the retractable member 114 to retract rapidly. In some examples, the biasing member 118 has a compression constant ranging from about 1.5 N/cm to about 3.5 N/cm.

In some embodiments, given that the biasing member 118 is compressed by a retraction distance $d_R$, a force contributed by the biasing member 118 may range from about 15.0 N to 35.0 N. In one example, the force of the compressed biasing member 118 in the retractable member 114 when the retractable member 114 is positioned in the guarded position can be about 22.0 N. When the biasing member 118 is installed in the retractable member 114, the biasing member 118 is visible from outside through the upper limb bypass slot 162 and the bottom wall slot 147.

Referring to FIG. 10A, to assemble the retractable device 110, the rear end 160 of the retractable member 114 can be inserted into the opening at the front end 185 of the sheath member 112, with the upper limb bypass slot 162 of the retractable member 114 aligned with the latch introduction slot 167 of the sheath member 112. The retractable member 114 can then be slidably moved toward the rear end 189 of the sheath member 112 during which the rear wall slot 148 formed in the rear wall 161 of the retractable member 114 slides past the compression member 180 on the sheath member 112, and the top wall of the retractable member 114 slides past the gap 190. When the rear end 166 of the upper limb bypass slot 162 of the retractable member 114 slides past the rear end 171 of the latch introduction slot 167 of the sheath member 112, the upper limb bypass slot 162 can be lined up with the latch introduction slot 167. The latch member 116 can then be introduced from the overlapped slots 167, 162 into the interior space of the retractable member 114. The rear end 160 of the retractable member 114 can then be pushed forward, allowing the top surface 129 of the release button 126 to abut the inner wall surface on the top side of the sheath member 112 and the lower end of the 144 of the latch member 116 to abut the inner wall surface of the bottom side of the sheath member 112.

The assembler can then pull the rear end 160 of the retractable member 114 rearwardly until the front end 164 of the upper limb bypass slot 162 engages with the front surface 125 of the release button 126 of the latch member 116, and then pull the retractable member 114 further rearwardly, pushing the latch member 116 to move rearwardly until the release button 126 of the latch member 116 snaps through the latch button slot 173 of the sheath member 112 due to the resilience force of the latch member 116, as shown in FIG. 10B. As a result, the release button 126 is self-secured in the button slot 173 of the sheath member 112, as a permanent location. In such circumstances, the detent element 132 of the latch member 116 is visible from above the sheath detent opening 179 of the sheath member 112.

The assembler then turns around the retractable device 110, allowing the bottom side of the retractable device 110 to face the assembler, with the biasing member introduction slot 149 at least partially exposed outside of the sheath member 112. The assembler can then insert and force the spring into the biasing member introduction slot 149.

The retractable device 110 can be disassembled following a reverse procedure of the assembling process of the retractable device 110.

In some embodiments, the tool head 150 can be replaced by any type of tool heads, such as various types of standard scalpel blades. In replacing the tool head 150, the tool head 150 is simply removed from front end of the tool head retention element 154.

When the retractable device 110 is in use, as depicted in FIG. 3A, in some embodiments, the retractable member 114 is pushed forward, allowing the tool head 150 to extend out from the front end of the sheath member 112 in the exposed position. The biasing member 118 is compressed accordingly. The locking bridge 168 of the support member 152 moves forward relative to the sheath member 112 until contact is made with the detent ramp 134 of the latch member 116. The locking bridge 168 of the support member 152 thus depresses the detent 132 of the latch member 116 downwardly. At the end of its travel, the locking bridge 168 of the support member 152 then contacts the locking slot 130. The resilience force of the latch member 116 disposes the upper limb 120 of the latch member 116 upwardly, thereby locking the retractable member 114 in its exposed position.

After locking, the sheath detent opening 179 defined in the sheath member 112 is then in position directly over the detent apex receiving opening 172 of the support member 152, thereby allowing an unencumbered upward travel of the detent 132 of the latch member 116 through both slots to achieve secure locking. When the retractable device 110 is not in use, the release button 126 of the latch member 116 is pressed, and the locking bridge 168 of the retractable member 114 is released from the engagement with the detent element 132 of the latch member 116 so as to allow the longitudinal movement between the sheath member 112 and the retractable member 114. The biasing force of the biasing member 118 of the support member 152, such as a compressed force of a spring, then instantly retracts the retractable member 114, rendering the tool head 150 covered by the sheath member 112.

The deployment and retraction sequence of the retractable device 110 has to be smooth and unencumbered by friction between the biasing member 118 and the inner wall surface of the support member 152. This smooth action is allowed by the coupling between the compression member 180 and a front end of the biasing member 118.

Figure 11:
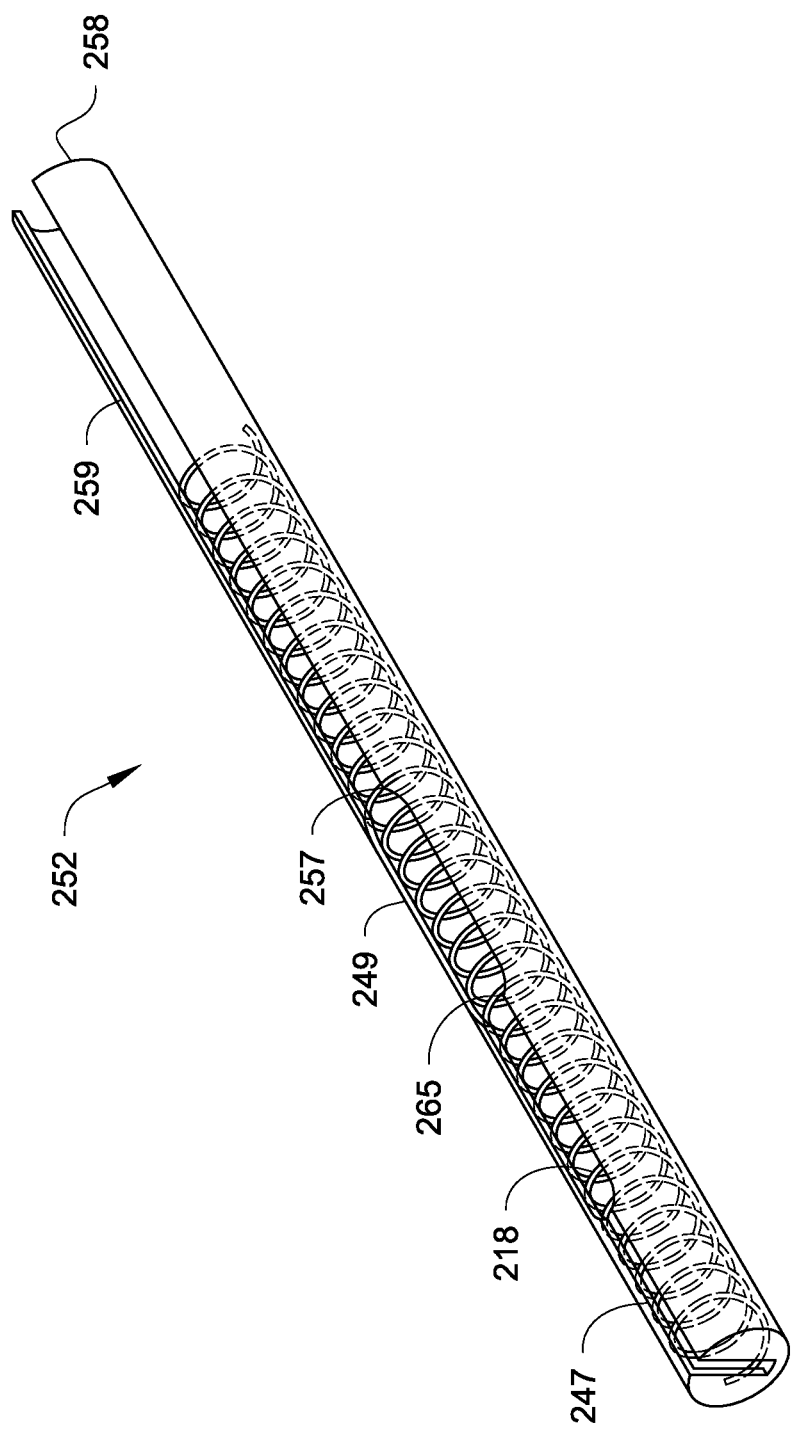
FIG. 11 is a perspective view showing a further embodiment of the retractable member with a biasing member disposed therein.

FIG. 11 shows a further embodiment of a support member 252 of the retractable member 214. The support member 252 has a similar configuration as the support member 152 except that a biasing member introduction slot 249 is located at a different location relative to the lower limb bypass slot 159 shown in FIGS. 6B and 7A-C.

As shown in FIG. 11, the support member 252 has a bottom wall slot 247 configured to allow the bottom wall of the support member 252 to bypass a compression member located on a sheath member. The support member 252 further has a lower limb bypass slot 259 configured to slide past a lower limb of a latch member when the retractable member moves between an exposed position and a guarded position relative to the sheath member. In the embodiment depicted in FIG. 11, a rear end 278 of the biasing member introduction slot 249 is connected directly with the bottom wall slot 247 instead of being connected with the lower limb bypass slot 259. Only the front end 257 of the biasing member introduction slot 249 is connected to the lower limb bypass slot 259. In such circumstances, the biasing member introduction slot 249 is at least partially exposed from the sheath member when the retractable member is positioned in both the exposed position and the guarded position. It is to be understood that the biasing member introduction slot 249 can be located at other locations relative to the lower limb bypass slot 259 and the bottom wall slot 247.

FIGS. 12A-B show a further embodiment of a sheath member 312. The sheath member 312 has a similar configuration as the sheath member 112 except that the sheath member 312 has a tool head maintaining mechanism 378. In such circumstances, the tool head maintaining mechanism 378 can be configured for safeguarding the tool head within the space defined by an outer wall surface 386 of the sheath member 312 without increasing the diameter of the sheath member 312.

In some embodiments, the tool head maintaining mechanism 378 can include a pair of longitudinally extending, diametrically opposed slots at a front portion of the sheath member 312. In some embodiments, the slots can include a top tool head slot 381 disposed at a top side of the sheath member 312 and a bottom tool head slot 383 disposed at a bottom side of the sheath member 312.

This configuration allows the retractable device to be used with a tool head that has a width slightly larger than the diameter of an inner wall surface 382 of the sheath member 312. The top slot 381 and the bottom slot 383 can be configured to allow a cutting edge of a larger tool head, such as a surgical blade, to be safely guarded in the sheath member 312, thereby protecting the tool head from accidental contact or injury to another person.

Figure 13A:
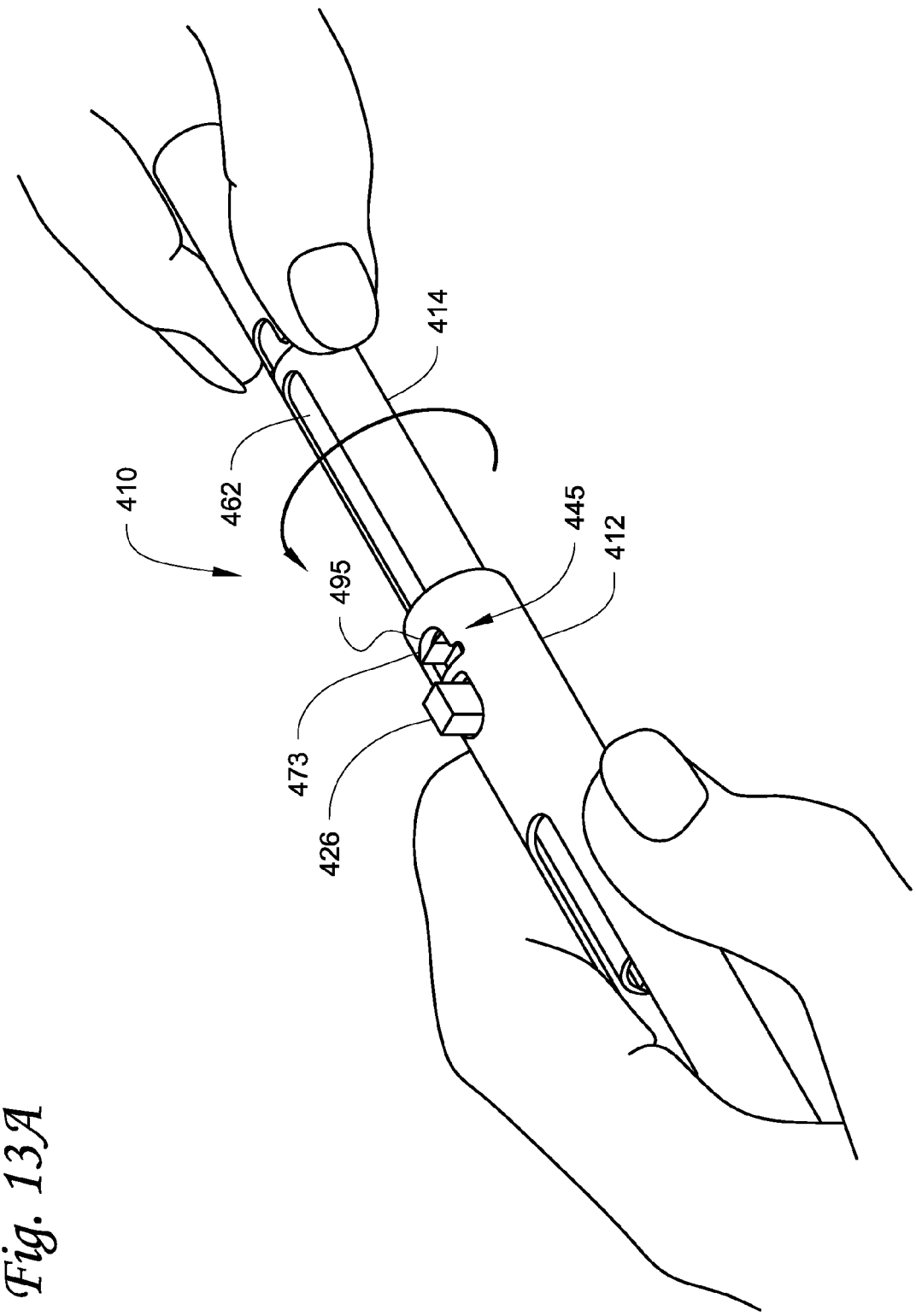
FIG. 13A is a perspective view of a yet further embodiment of a retractable device showing a locking mechanism.

Referring to FIGS. 13A-E, in some embodiments, a retractable device 410 can include a locking mechanism 445 to prevent a retractable member 414 from moving axially relative to a sheath member 412, when the retractable device 410 is positioned in the guarded position. For example, as shown in FIG. 13A, the locking mechanism 445 can be actuated by rotating the retractable member 414 relative to the sheath member 412 so as to lock the retractable member 414 axially relative to the sheath member 412, preventing the retractable member 414 from moving forward. The locking mechanism 445 can be released by counter-rotating the retractable member 414 relative to the sheath member 412. It is to be understood that the locking mechanism 445 can have other configurations as long as it can prevent axial movement of the retractable member 414 relative to a sheath member 412.

Referring to FIGS. 13B-C, the locking mechanism 445 can include cutouts formed on a support member 452 of the retractable member 414. For example, the locking mechanism 445 can include an upper limb cutout 443 formed on a left side of an upper limb bypass slot 462. The upper limb cutout 443 has a front end shoulder 494 located in a vicinity of a front end 458 of the slot 462, when viewed from above the upper limb bypass slot 462. In some embodiments, the term "vicinity" can mean a distance similar to or less than a width $W_{US}$ of the upper limb bypass slot 462.

The upper limb cutout 443 can have a width $W_{UC}$ configured to be slightly greater than a width W of the upper limb of a latch member 416 installed in the retractable member 414, similar to the width $W_{US}$ of the upper limb bypass slot 462. The length of the upper limb cutout 443 can be slightly longer than the distance between a front surface 425 of a release button 426 and a detent apex 433 of a detent element 432 of the latch member 416. It is to be understood that the width $W_{UC}$ and the length of the upper limb cutout 443 can vary as long as the upper limb cutout 443 is large enough to receive the release button 426 and at least part of the detent element 432 in a locked position as shown in FIG. 13A.

It is to be understood that the particular shape and location of the upper limb cutout 443 can vary. For example, the cutout 443 can be located on the right side, instead of the left side, of the upper limb bypass slot 462. The cutout 443 can also be located at other locations relative to the upper limb bypass slot 462, as long as the location and the shape of the cutout 443 allow the latch 416 to be received in the cutout 443, when the retractable member 414 is rotated relative to the sheath member 412.

Referring to FIGS. 13D-E, the locking mechanism 445 can also include a lower limb cutout 491 and a compression member cutout 493 formed on a left side of a lower limb bypass slot 459, when viewed from above the lower limb bypass slot 459. In such circumstances, the front end of the lower limb cutout 491 can be located on a slightly rear side of the front end of the upper limb cutout 443 to thereby receive a balancing element 440 of the latch member 416 when the retractable member 414 is in the locked position as shown in FIG. 13A.

The compression member cutout 493 is located on a rear side of the lower limb cutout 491. The compression member cutout 493 is configured to receive the lower end of a compression member (the lower end of the compression member is not shown in FIGS. 13A-E; referring to the lower end 192 in a similar embodiment in FIGS. 3A-B) formed on an inner surface of the sheath member 412, when the retractable member 414 is in the locked position.

Still referring to FIGS. 13D-E, the lower limb cutout 491 and the compression member cutout 493 can have a width slightly greater than a width W of the lower limb of the latch member 416 installed in the retractable member 414. The length of the lower limb cutout 491 can vary as long as it can snugly receive the balancing element 440. The length of the compression member cutout 493 can vary as long as it can snugly receive the lower end of the compression member of the sheath member 412.

It is to be understood that the particular location of the lower limb cutout 491 and the compression member cutout 493 can vary. For example, the cutouts 491, 493 can be located on the right side, instead of the left side, of the lower limb bypass slot 459. The cutouts 491, 493 can also be located at other locations relative to the lower limb bypass slot 459, as long as the location and the shape of the cutouts 491, 493 allow the balancing element 440 of the latch 416 and the lower end of the compression member to be received in the cutouts 491, 493, respectively, when the retractable member 414 is rotated relative to the sheath member 412.

It is to be understood that the width of the upper limb cutout 443, the width of the lower limb cutout 491 and the width of the compression member cutout 493 can vary. When the width of the upper limb cutout 443, the width of the lower limb cutout 491 and the width of the compression member cutout 493 are greater, the retractable member 414 can be rotated a greater angle relative to the sheath member 412. When the width of the upper limb cutout 443, the width of the lower limb cutout 491 and the width of the compression member cutout 493 are smaller, the retractable member 414 can be rotated less relative to the sheath member 412. In some embodiments, the retractable member 414 is configured to rotate 30° relative to the sheath member 412. In other embodiments, the retractable member 414 is configured to rotate less than 30°, such as 15° relative to the sheath member.

Referring to FIG. 13A, to actuate the locking mechanism 445 of the retractable device 410, the retractable member 414 can be rotated counter-clockwise relative to the sheath member 412 (when viewed from the front side of the retractable member 414), when the retractable device 410 is positioned in a guarded position. In such circumstances, the upper limb cutout 443 is aligned with the release button slot 473. As a result, the retractable member 414 is locked axially relative to the sheath member 412, preventing the retractable member 414 from moving forward. The locking mechanism 445 can be released by rotating the retractable member 414 clockwise (when viewed from the front side of the retractable member 414) to allow the release button 426 to be released from the upper limb cutout 443.

As shown in FIG. 13A-C, in some embodiments, the front end shoulder 494 of the upper limb cutout 443 is located on a slightly rear side of the front end 458 of the upper limb bypass slot 462 of the support member 452. For example, the front end shoulder 494 of the upper limb cutout 443 can be located 1/16 inches on the rear side of the front end 458 of the upper limb bypass slot 462.

To actuate the locking mechanism 445, the retractable device 410 is initially positioned in the guarded position. The retractable member 414 is then pushed slightly forward. Once the front end shoulder 494 of the upper limb cutout 443 of the retractable member 414 is aligned with the front end 495 of a latch button slot 473 of the sheath member 412, the retractable member 414 is rotated counter-clockwise relative to the sheath member 412 (when viewed from the front side of the retractable member 414) such that the upper limb cutout 443 is aligned with the release button slot axially. As a result, the upper limb bypass slot 462 of the support member 452 is rotated sideway and no longer aligned with the release button slot 473 of the sheath member. The fact that the front end shoulder 494 of the upper limb cutout 443 is located on a rear side of the front end 458 of the upper limb bypass slot 462 allows a positive engagement between the upper limb cutout 443 and the release button 426. The locking mechanism 445 can be released by rotating the retractable member 414 clockwise (when viewed from the front side of the retractable member 414) to allow the release button 426 to be released from the upper limb cutout 443.

FIGS. 14A-F illustrate a retractable device 510 similar to the configuration of FIGS. 13A-E, except that a locking mechanism 545 of the retractable device 510 has a different design. As shown in FIGS. 14A-D, the locking mechanism 545 can include cutouts formed on a support member 552 of a retractable member 514 and a locking status indicator 515. It is to be understood that the locking mechanism 545 can have other configurations as long as it can prevent axial movement of the retractable member 514 relative to a sheath member 512 and indicate the locking status.

As shown in FIGS. 14C-D, the locking mechanism 545 can include an upper limb cutout 543 formed on a left side of an upper limb bypass slot 562. The upper limb cutout 543 has a front end shoulder 594 formed by radially extending a front end 558 of the slot 562 toward a left side. When viewed from above the upper limb bypass slot 562, the front end shoulder 594 of the cutout 543 and the front end 558 of the slot 562 end at the same axial location on the retractable member 514.

The upper limb cutout 543 can have a width $W_{UC}$ configured to be slightly greater than the width W of the upper limb of a latch member 516 installed in the retractable member 514, similar to a width $W_{US}$ of the upper limb bypass slot 562. The length of the upper limb cutout 543 can be slightly longer than the distance between a front surface 525 of a release button 526 and a detent apex 533 of a detent element 532 of the latch member 516. It is to be understood that the width $W_{UC}$ and the length of the upper limb cutout 543 can vary as long as the upper limb cutout 543 is large enough to receive the release button 526 and at least part of the detent element 532 in a locked position as shown in FIG. 14A-B.

It is to be understood that the particular location of the upper limb cutout 543 can vary. For example, the cutout 543 can be located on the right side, instead of the left side, of the upper limb bypass slot 562. The cutout 543 can also be located at other locations relative to the upper limb bypass slot 562, as long as the location and the shape of the cutout 543 allows the latch 516 to be received in the cutout 543, when the retractable member 514 is rotated relative to the sheath member 512.

Figure 14A:
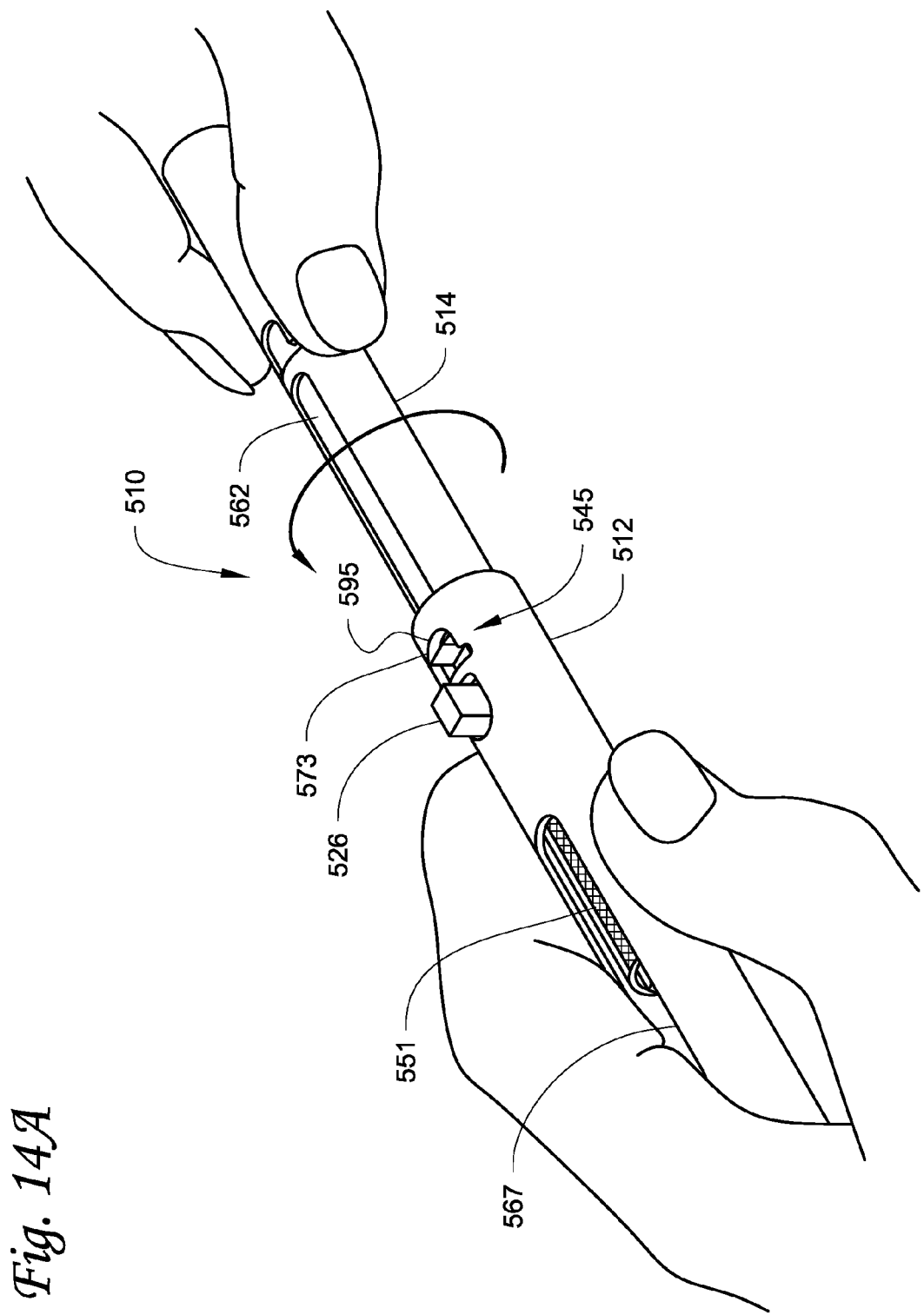
FIG. 14A is a perspective view of an even further embodiment of a retractable device in an unlocked position.
Figure 14B:
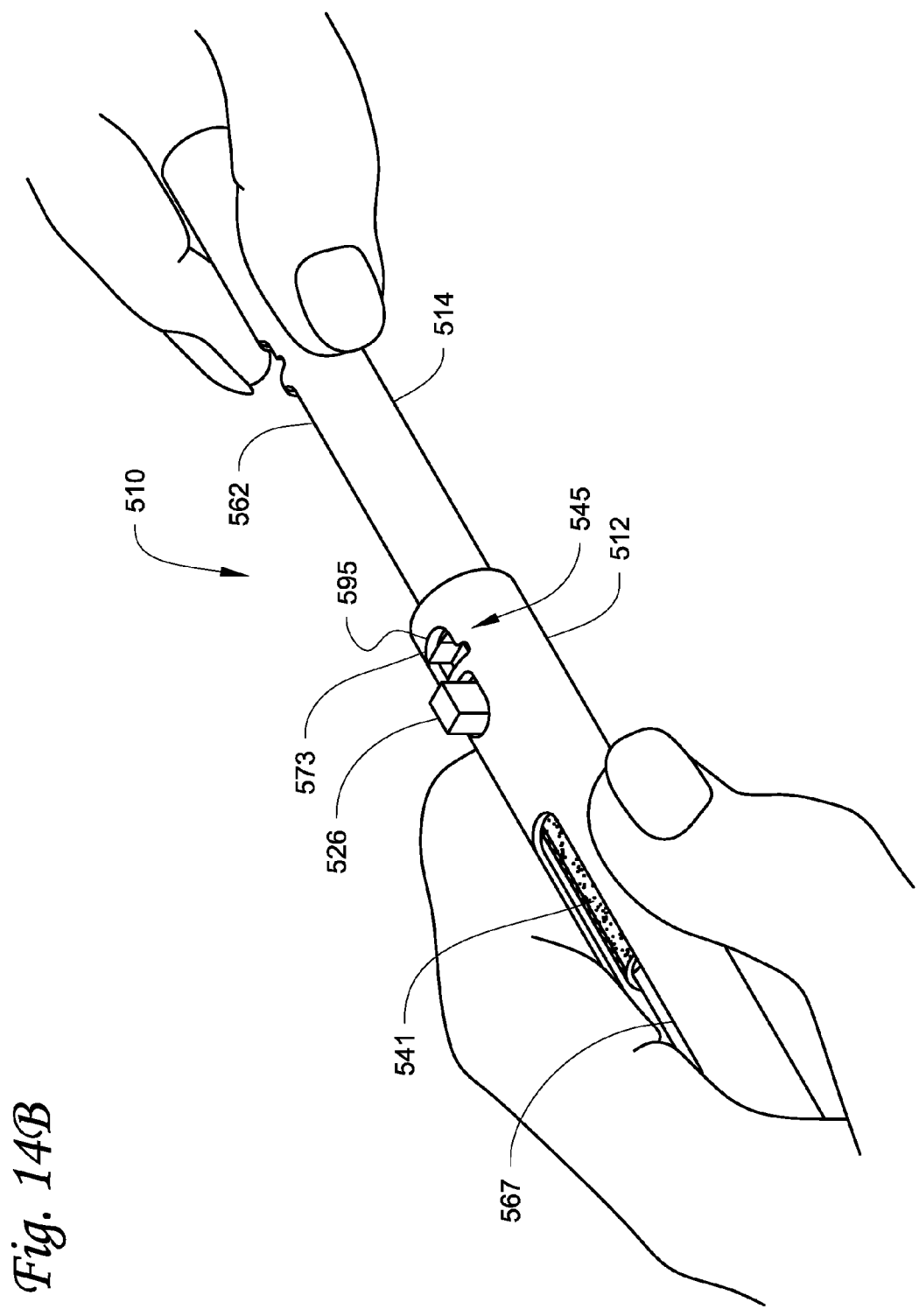
FIG. 14B is a perspective view of the retractable device of FIG. 14A in a locked position.

Referring to FIGS. 14E-F, the locking mechanism 545 can also include a lower cutout 591 formed on a left side of a lower limb bypass slot 559 of the support member 552 of the retractable member 514, when viewed from above the lower limb bypass slot 559. In such circumstances, the front end of the lower cutout 591 can be located on a slightly rear side of the front end of the upper limb cutout 543, and the length of the lower cutout 591 can be configured to snugly contain both a balancing element 540 of the latch member 516 and the lower end of a compression member formed on an inner surface of the sheath member 512 (the lower end of the compression member is not shown in FIGS. 14A-F; referring to the lower end 192 in a similar embodiment in FIGS. 3A-B), when the retractable member 514 is in the locked position as shown in FIG. 14A-B.

Still referring to FIGS. 14E-F, the lower cutout 591 can have a width slightly greater than the width of the lower limb of the latch member 516 installed in the retractable member 514 and the width of the lower end of the compression member formed on the sheath member 512.

It is to be understood that the particular location of the lower cutout 591 can vary. For example, the cutout 591 can be located on the right side, instead of the left side, of the lower limb bypass slot 559. The cutout 591 can also be located at other locations relative to the lower limb bypass slot 559, as long as the location and the shape of the cutout 591 allow the balancing element 540 of the latch 516 and the lower end of the compression member to be received in the cutout 591, when the retractable member 514 is rotated relative to the sheath member 512.

It is to be understood that the width of the upper limb cutout 543 and the width of the lower cutout 591 can vary. When the width of the upper limb cutout 543 and the width of the lower cutout 591 are greater, the retractable member 514 can be rotated a greater angle relative to the sheath member 512. When the width of the upper limb cutout 543 and the width of the lower cutout 591 are smaller, the retractable member 514 can be rotated less relative to the sheath member 512. In some embodiments, the retractable member 514 is configured to rotate 45° relative to the sheath member 512. In other embodiments, the retractable member 514 is configured to rotate less than 45°, such as 30° or 15° relative to the sheath member.

With the width extension, the upper limb bypass slot 562 along with the upper limb cutout 543 can act as a biasing member introduction slot 549 that allows a biasing member, such as a spring, to be introduced. In such circumstances, the length and width of the biasing member introduction slot 549 are configured to be as small as possible to decrease the chance of disfigurement of the biasing member during compression, as long as the length and width of the biasing member introduction slot 549 are great enough for introduction of the biasing member. This can help reduce uneven compression of the biasing member.

Likewise, with the width extension, the lower limb bypass slot 559 along with the lower cutout 591 can act as a biasing member introduction slot 549 that allows a biasing member, such as a spring, to be introduced. In such circumstances, the length and width of the biasing member introduction slot 549 are configured to be as small as possible to decrease the chance of disfigurement of the biasing member during compression, as long as the length and width of the biasing member introduction slot 549 are great enough for introduction of the biasing member. This can help reduce uneven compression of the biasing member.

The locking mechanism 545 of the retractable device 510 depicted in FIGS. 14A-E includes a locking status indicator 515. The locking status indicator 515 can be configured to indicate a status of the locking mechanism 545, for example, whether the retractable device 510 is locked in a guarded position. In some embodiments, the locking status indicator 515 can be a reference component to which a user can refer to decide a detectable condition of the retractable device 510.

Referring to FIGS. 14C-D, in some embodiments, color coding can be used as at least part of the locking status indicator 515. In the embodiment depicted in FIGS. 14A-F, a front portion of the support member 552 of the retractable member 514 can be colored with a particular color, for example, red, as a reference component 541 showing that the retractable device 510 has been locked. As shown in FIG. 14B, when the retractable device 510 is locked, the reference component 541 can be viewed through the upper limb bypass slot 562 of the sheath member 512. The color coding of the reference component 541 can indicate that the retractable device 510 is locked in the guarded position.

In some embodiments, as shown in FIGS. 14C-D, a further reference component 551 can be indicated on the front portion of the support member 552 of the retractable member 514, next to the reference component 541. The reference component 551 can include a different color, for example, green, to indicate that the retractable device has been unlocked. As shown in FIG. 14A, when the retractable device 510 is unlocked, the reference component 551 can be viewed through the upper limb bypass slot 562 of the sheath member 512. The color coding of the reference component 551 can indicate that the retractable device 510 is unlocked.

It is to be understood that the particular color of the reference components 541, 551 can vary as desired. It is also to be understood that in some embodiments, the reference component 551 is not needed to indicate the unlocked status.

In some embodiment, indicia can be used either alone or in combination with the color coding, as at least part of the locking status indicator 515. For example, when red is used for the reference component 541 to indicate the retractable device 510 being in a locked status, the indicia "LOCKED" can be added as part of the reference component 541. As a result, the reference component 541 includes both the color coding and the indicia to show that the retractable device 510 has been locked. In such circumstances, the reference component 541, e.g., the indicia "LOCKED" in red color, can be viewed through the upper limb bypass slot 562 of the sheath member 512.

Likewise, when green is used for the reference component 551 to indicate the retractable device 510 being in an unlocked status, the indicia "UNLOCKED" can be added as part of the reference component 551. As a result, the reference component 551 includes both the color coding and the indicia to show that the retractable device 510 has been unlocked. In such circumstances, the reference component 551, e.g., the indicia "UNLOCKED" in green color, can be viewed through the upper limb bypass slot 562 of the sheath member 512.

Similar to the process depicted in FIG. 10A and the accompanying text, as shown in FIGS. 14A-F, to assemble the retractable device 510, the rear end of the retractable member 514 can be inserted into the opening at the front end of the sheath member 512, with the upper limb bypass slot 562 of the retractable member 514 aligned with a latch introduction slot 567 of the sheath member 512. The retractable member 514 can then be slidably moved toward the rear end of the sheath member 512 during which the rear wall slot formed in the rear wall of the retractable member 514 slide past the compression member on the sheath member 512, and the top wall of the retractable member 514 slides past the gap formed between the compression member and the inner surface of the sheath member 512. When the rear end of the retractable member 514 slides past the rear end of the sheath member and any of the biasing member introduction slots 549 defined in the top or bottom wall of the support member 552 of the retractable member 514 is exposed, the assembler can then insert and force a biasing member, e.g., a spring, into the respective biasing member introduction slot 549.

The assembler can then push the rear end of the retractable member 514 forward relative to the sheath member 512 until the front end of the upper limb bypass slot 562 of the retractable member 514 slides past the rear end of the latch introduction slot 567 of the sheath member 512. The assembler can then align the upper limb bypass slot 562 with the latch introduction slot 567 to allow the latch member 516 to be introduced into the interior space of the retractable member 514 through the overlapped slots 567, 562.

The latch member 516 can then be pressed downwardly and rearwardly to allow the top surface of the release button 526 to abut the inner wall surface on the top side of the sheath member 512 and the lower end of the latch member 516 to abut the inner wall surface of the bottom side of the sheath member 512. The assembler can then pull the rear end of the retractable element 514 rearwardly until the front end of the upper limb bypass slot 562 engages with the front surface of the release button 526 of the latch member 516, and then pull the retractable member 514 further rearwardly, pushing the latch member 516 to move rearwardly until the release button 526 of the latch member 516 snaps through the latch button slot 573 of the sheath member 512 due to the resilience force of the latch member 516, as shown in FIG. 14A. As a result, the release button 526 is self-secured in the button slot 573 of the sheath member 512, as a permanent location. In such circumstances, the detent element 532 of the latch member 516 is visible to a viewer.

The retractable device 510 can be disassembled following a reverse procedure of the assembling process of the retractable device 510.

Referring to FIGS. 14A-B, to actuate the locking mechanism 545 of the retractable device 510, the retractable member 514 can be rotated counter-clockwise relative to the sheath member 512 (when viewed from the front side of the retractable member 514), when the retractable device 510 is positioned in the guarded position. In such circumstances, the upper limb cutout 543 is aligned with the release button slot 573. As a result, the retractable member 514 is locked axially relative to the sheath member 512, preventing the retractable member 514 from moving forward. The reference component 541 of the locking status indicator 515 can be viewed by the user through the upper limb bypass slot 562 to indicate that the retractable device 510 is locked in the guarded position. The locking mechanism 545 can be released by rotating the retractable member 514 clockwise (when viewed from the front side of the retractable member 514) to allow the release button 526 to be released from the upper limb cutout 543. In such circumstances, the reference component 551 of the locking status indicator 515 can be viewed by the user through the upper limb bypass slot 562 to indicate that the retractable device 510 is unlocked.

Aspects:

The following numbered aspects provide further disclosure of the application. It is noted that any of aspects 1-12 below can be combined with any of aspects 13-19 and any of aspects 20-21. Also, any of aspects 13-19 below can be combined with any of aspects 20-21.

1. A retractable surgical knife, comprising:
   a sheath member having front and rear ends;
   a retractable member including a support member and a blade supported by the support member, wherein the support member has a front end, a rear end and an elongated interior space; the retractable member being partially disposed in the sheath member and telescopically received in the sheath member for movement between an guarded position wherein the blade is guarded in the sheath member, and an exposed position wherein the blade extends out of the sheath member;
   top and bottom elongated and longitudinally extended slots formed on the support member, wherein the top slot is disposed along a top side of the support member and the bottom slot is disposed along a bottom side of the support member,
   a top opening defined in the top side of the sheath member;
   a biasing member disposed in the interior space of the support member;
   a latch member disposed in the interior space of the support member, the latch member having a release button projecting through the top opening of the sheath member and the top slot of the support member, and a bottom section projecting through the bottom slot of the support member and abut the inner surface of the sheath member; and
   a locking mechanism configured to lock the retractable member relative to the sheath member in an axial direction in the guarded position;
   wherein the locking mechanism comprises a locking status indicator that includes a reference component disposed on an outer surface of the support member that is viewable to a viewer, when the retractable device is locked in the guarded position.

2. The retractable surgical knife of claim 1, wherein the locking mechanism comprises a top cutout and a bottom cutout defined in the top side and the bottom side of the support member, respectively; the top cutout and the bottom cutout extending in a same clockwise or counter-clockwise direction circumferentially from a side edge of the top slot and a side edge of the bottom slot, respectively, thereby allowing the latch member to be received in the cutouts when the retractable member is rotated relative to the sheath member.

3. The retractable surgical knife of claim 2, wherein the top cutout includes a front end shoulder with which the latch member engages when the retractable member is locked in the guarded position.

4. The retractable surgical knife of claim 3, wherein the front end shoulder of the top cutout and the front end of the top slot of the support member end at the same axial location.

5. The retractable surgical knife of claim 3, wherein the front end shoulder of the top cutout is located slightly rearwardly than the front end of the top slot on the support member.

6. The retractable surgical knife of any of claims 1-5, wherein the reference component is color coding, indicia or a combination thereof.

7. The retractable surgical knife of any of claims 1-6, wherein the sheath member, the support member and the latch member are all made of non-metal materials.

8. The retractable surgical knife of any of claims 1-7, wherein the biasing member is made of non-metal material.

9. The retractable surgical knife of any of claims 1-8, wherein the latch member is made of non-metal material.

10. The retractable surgical knife of any of claims 1-9, further comprising: a compression member attached to the rear end of the sheath member and tapered rearwardly from the rear end of the sheath member, the compression member being configured to bias the biasing member toward the rear end of the support member, wherein the rear end of the support member has a slot that allows the compression member to pass by, thereby allowing the rear end of support member to pass an entire length of the sheath member 11. The retractable surgical knife of any of claims 1-10, wherein the sheath member has a pair of longitudinally extending, diametrically opposed slots located at a front portion of the sheath member, thereby allowing the sheath member to safeguard a blade having a width larger than an inner diameter but smaller than an outer diameter of the sheath member.

12. The retractable surgical knife of any of claims 1-11, wherein the support member includes a locking bridge having a beveled edge, the beveled edge being configured to allow the locking bridge to slide over a detent ramp of the detent element of the latch member to reduce friction.

13. A retractable tool holder, comprising:
    a sheath member having front and rear ends;
    a retractable member including a support member and a tool head retention element supported by the support member, wherein the support member having an elongated interior space; the retractable member being partially disposed in the sheath member, and telescopically received in the sheath member for movement between a guarded position wherein the tool head retention element is retracted into the sheath member, and an exposed position wherein the tool head retention element extends out of the sheath member;

top and bottom elongated and longitudinally extended slots formed on the support member wherein the top slot is disposed along a top side of the support member and the bottom slot is disposed along a bottom side of the support member,
a top opening defined in the top side of the sheath member;
a biasing member disposed in the interior space of the support member; and
a latch member for latching the retractable member in the exposed position, the latch member having a release button being receivable in the top opening of the sheath member and the top slot of the support member, thereby locking the sheath member and the support member against further relative movement; and
a locking mechanism configured to lock the retractable member relative to the sheath member in an axial direction,
wherein the locking mechanism further comprises a locking status indicator, wherein the locking status indicator includes a reference component disposed on an outer surface of the support member that is viewable to a viewer, when the retractable device is locked in the guarded position.

14. The retractable tool holder of claim 13, wherein the locking mechanism comprises a top cutout and a bottom cutout defined in the top side and the bottom side of the support member, respectively; the top cutout and the bottom cutout extending in a same clockwise or counterclockwise direction circumferentially from a side edge of the top slot and a side edge of the bottom slot, respectively, thereby allowing the latch member to be received in the cutouts when the retractable member is rotated relative to the sheath member.

15. The retractable tool holder of claim 14, wherein the top cutout includes a front end shoulder with which the latch member engages when the retractable member is locked in the guarded position.

16. The retractable tool holder of claim 15, wherein the front end shoulder of the top cutout and the front end of the top slot of the support member end at the same axial location.

17. The retractable tool holder of claim 15, wherein the front end shoulder of the top cutout is located slightly rearwardly than the front end of the top slot on the support member.

18. The retractable tool holder of any of claims 13-17, wherein the reference component is color coding, indicia or a combination thereof.

19. The retractable tool holder of any of claims 13-18, further comprising: a compression member attached to the rear end of the sheath member and tapered rearwardly from the rear end of the sheath member, the compression member being configured to bias the biasing member toward the rear end of the support member, wherein the rear end of the support member has a slot that allows the compression member to pass by, thereby allowing the rear end of support member to pass an entire length of the sheath member 20. A retractable device, consisting essentially of:
a sheath member including a front end, a back end and a top opening defined in a top side of the sheath member;
a retractable member including a support member and a tool head supported by the support member, wherein the support member having an elongated interior space; the retractable member being partially disposed in the sheath member, and telescopically received in the sheath member for movement between a guarded position wherein the tool head retention element is retracted into the sheath member, and an exposed position wherein the tool head retention element extends out of the sheath member; the support member including a top and a bottom elongated and longitudinally extended slots wherein the top slot is disposed along a top side of the support member and the bottom slot is disposed along a bottom side of the support member;
a biasing member disposed in the interior space of the support member; and
a latch member for latching the support member in the exposed position, the latch member having a release button being receivable in the top opening of the sheath member and the top slot of the support member, thereby locking the sheath member and the support member against further relative movement
wherein the retractable device include only the sheath member, the retractable member, the biasing member and the latch member that movable relative to each other.

21. The retractable device of claim 20, further comprising:
a compression member attached to the rear end of the sheath member and tapered rearwardly from the rear end of the sheath member, the compression member being configured to bias the biasing member toward the rear end of the support member, wherein the rear end of the support member has a slot that allows the compression member to pass by, thereby allowing the rear end of support member to pass an entire length of the sheath member.

The described embodiments are to be considered in all respects only as illustrative and not restrictive. The scope of the invention is therefore, indicated by the appended claims rather than by the foregoing description. All changes which come within the meaning and range of equivalency of the claims are to be embraced within their scope.

What is claimed is:

1. A retractable surgical knife, comprising:
a sheath member having front and rear ends;
a retractable member including a support member and a blade supported by the support member, wherein the support member has a front end, a rear end and an elongated interior space; the retractable member being partially disposed in the sheath member and telescopically received in the sheath member for movement between a guarded position wherein the blade is guarded in the sheath member, and an exposed position wherein the blade extends out of the sheath member;
top and bottom elongated and longitudinally extended slots formed on the support member, wherein the top slot is disposed along a top side of the support member and the bottom slot is disposed along a bottom side of the support member,
a top opening defined in a top side of the sheath member;
a biasing member disposed in the interior space of the support member;
a latch member disposed in the interior space of the support member, the latch member having a release button projecting through the top opening of the sheath member and the top slot of the support member, and a bottom section projecting through the bottom slot of the support member and abut the inner surface of the sheath member; and
a locking mechanism configured to lock the retractable member relative to the sheath member in an axial direction in the guarded position;

wherein the locking mechanism comprises a locking status indicator that includes a reference component disposed on an outer surface of the support member that is viewable to a viewer, when the retractable surgical knife is locked in the guarded position.

2. The retractable surgical knife of claim 1, wherein the locking mechanism comprises a top cutout and a bottom cutout defined in the top side and the bottom side of the support member, respectively; the top cutout and the bottom cutout extending in a same clockwise or counterclockwise direction circumferentially from a side edge of the top slot and a side edge of the bottom slot, respectively, thereby allowing the latch member to be received in the cutouts when the retractable member is rotated relative to the sheath member.

3. The retractable surgical knife of claim 1, wherein the top cutout includes a front end shoulder with which the latch member engages when the retractable member is locked in the guarded position.

4. The retractable surgical knife of claim 1, wherein the front end shoulder of the top cutout and a front end of the top slot of the support member end at the same axial location.

5. The retractable surgical knife of claim 3, wherein the front end shoulder of the top cutout is located slightly rearwardly than the front end of the top slot on the support member.

6. The retractable surgical knife of claim 1, wherein the reference component is color coding, indicia or a combination thereof.

7. The retractable surgical knife of claim 1, further comprising: a compression member attached to the rear end of the sheath member and tapered rearwardly from the rear end of the sheath member, the compression member being configured to bias the biasing member toward a rear end of the support member, wherein the rear end of the support member has a slot that allows the compression member to pass by, thereby allowing the rear end of the support member to pass an entire length of the sheath member.

8. The retractable surgical knife of claim 1, wherein the sheath member has a pair of longitudinally extending, diametrically opposed slots located at a front portion of the sheath member, thereby allowing the sheath member to safeguard the blade having a width larger than an inner diameter but smaller than an outer diameter of the sheath member.

9. A retractable tool holder, comprising:
a sheath member having front and rear ends;
a retractable member including a support member and a tool head retention element supported by the support member, wherein the support member having an elongated interior space; the retractable member being partially disposed in the sheath member, and telescopically received in the sheath member for movement between a guarded position wherein the tool head retention element is retracted into the sheath member, and an exposed position wherein the tool head retention element extends out of the sheath member;
top and bottom elongated and longitudinally extended slots formed on the support member wherein the top slot is disposed along a top side of the support member and the bottom slot is disposed along a bottom side of the support member,
a top opening defined in a top side of the sheath member;
a biasing member disposed in the interior space of the support member; and
a latch member for latching the retractable member in the exposed position, the latch member having a release button being receivable in the top opening of the sheath member and the top slot of the support member, thereby locking the sheath member and the support member against further relative movement; and
a locking mechanism configured to lock the retractable member relative to the sheath member in an axial direction,
wherein the locking mechanism further comprises a locking status indicator, wherein the locking status indicator includes a reference component disposed on an outer surface of the support member that is viewable to a viewer, when the retractable tool holder is locked in the guarded position.

10. The retractable tool holder of claim 9, wherein the locking mechanism comprises a top cutout and a bottom cutout defined in the top side and the bottom side of the support member, respectively; the top cutout and the bottom cutout extending in a same clockwise or counterclockwise direction circumferentially from a side edge of the top slot and a side edge of the bottom slot, respectively, thereby allowing the latch member to be received in the cutouts when the retractable member is rotated relative to the sheath member.

11. The retractable tool holder of claim 10, wherein the top cutout includes a front end shoulder with which the latch member engages when the retractable member is locked in the guarded position, wherein the front end shoulder of the top cutout is located slightly rearwardly than the front end of the top slot on the support member.

12. The retractable tool holder of claim 9, wherein the reference component is color coding, indicia or a combination thereof.

13. The retractable tool holder of claim 9, further comprising: a compression member attached to the rear end of the sheath member and tapered rearwardly from the rear end of the sheath member, the compression member being configured to bias the biasing member toward a rear end of the support member, wherein the rear end of the support member has a slot that allows the compression member to pass by, thereby allowing the rear end of the support member to pass an entire length of the sheath member.

14. A retractable device, consisting essentially of:
a sheath member including a front end, a back end and a top opening defined in a top side of the sheath member;
a retractable member including a support member and a tool head supported by the support member, wherein the support member having an elongated interior space; the retractable member being partially disposed in the sheath member, and telescopically received in the sheath member for movement between a guarded position wherein a tool head retention element is retracted into the sheath member, and an exposed position wherein the tool head retention element extends out of the sheath member; the support member including a top and a bottom elongated and longitudinally extended slots wherein the top slot is disposed along a top side of the support member and the bottom slot is disposed along a bottom side of the support member;
a biasing member disposed in the interior space of the support member; and
a latch member for latching the support member in the exposed position, the latch member having a release button being receivable in the top opening of the sheath member and the top slot of the support member, thereby locking the sheath member and the support member against further relative movement; and a compression member attached to the back end of the sheath member and tapered rearwardly from the back end of the sheath member, the compression member being configured to bias the biasing member toward a rear end of the support member, wherein the rear end of the support member has a slot that allows the compression member to pass by, thereby allowing the rear end of the support member to pass an entire length of the sheath member, and wherein the retractable device include only the sheath member, the retractable member, the biasing member and the latch member that are movable relative to each other.

* * * * *